United States Patent
Wilson et al.

(10) Patent No.: US 10,531,851 B2
(45) Date of Patent: Jan. 14, 2020

(54) DUAL ENERGY X-RAY CORONARY CALCIUM GRADING

(71) Applicant: Case Western Reserve University, Cleveland, OH (US)

(72) Inventors: David Wilson, Cleveland Heights, OH (US); Robert Gilkeson, Cleveland Heights, OH (US); Di Wen, Cleveland Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 109 days.

(21) Appl. No.: 15/729,824

(22) Filed: Oct. 11, 2017

(65) Prior Publication Data
US 2018/0042565 A1    Feb. 15, 2018

Related U.S. Application Data

(63) Continuation of application No. PCT/US2016/027127, filed on Apr. 12, 2016.
(Continued)

(51) Int. Cl.
*A61B 6/00* (2006.01)
*A61B 6/03* (2006.01)
(Continued)

(52) U.S. Cl.
CPC ............ *A61B 6/482* (2013.01); *A61B 5/0402* (2013.01); *A61B 6/032* (2013.01); *A61B 6/405* (2013.01);
(Continued)

(58) Field of Classification Search
None
See application file for complete search history.

(56) References Cited

U.S. PATENT DOCUMENTS 4,542,459 A * 9/1985 Riederer .............. H04N 5/3205
                                                    348/E5.089
8,249,815 B2 * 8/2012 Taylor ................ A61B 5/02007
                                                        702/19
(Continued)

FOREIGN PATENT DOCUMENTS

JP      H08336517 A    12/1996
JP      2007007255 A    1/2007
(Continued)

OTHER PUBLICATIONS

Išgum, Ivana, et al. "Detection of coronary calcifications from computed tomography scans for automated risk assessment of coronary artery disease." Medical physics 34.4 (2007): 1450-1461. (Year: 2007).*

(Continued)

*Primary Examiner* — Michelle M Entezari
(74) *Attorney, Agent, or Firm* — Eschweiler & Potashnik, LLC

(57) ABSTRACT

Methods and apparatus for grading coronary calcium, including an example apparatus that includes a set of logics and a memory that stores a set of radiographic images. The set of logics includes an image acquisition logic that acquires a set of radiographic images of a region of tissue, the set of radiographic images including a low-energy reference x-ray image and a higher-energy floating x-ray image, a registration logic that produces a set of registered images from a plurality of members of the set of radiographic images, an enhancement logic that produces a set of calcium-enhanced images from the set of registered images, a post-enhancement logic that produces a bone image from the set of calcium-enhanced images, and a grading logic that computes a coronary heart disease prediction score based, at (Continued)

least in part, on the bone image and a set of features extracted from the bone image.

22 Claims, 12 Drawing Sheets

Related U.S. Application Data

(60) Provisional application No. 62/146,442, filed on Apr. 13, 2015.

(51) Int. Cl.

| | |
|---|---|
| *G06T 5/50* | (2006.01) |
| *G06T 7/11* | (2017.01) |
| *G06T 7/13* | (2017.01) |
| *G06T 3/00* | (2006.01) |
| *G06T 5/00* | (2006.01) |
| *G06T 5/20* | (2006.01) |
| *G06T 7/00* | (2017.01) |
| *A61B 5/0402* | (2006.01) |

(52) U.S. Cl.
CPC .............. *A61B 6/503* (2013.01); *A61B 6/504* (2013.01); *A61B 6/5217* (2013.01); *A61B 6/5258* (2013.01); *A61B 6/541* (2013.01); *G06T 3/0068* (2013.01); *G06T 5/009* (2013.01); *G06T 5/20* (2013.01); *G06T 5/50* (2013.01); *G06T 7/0014* (2013.01); *G06T 7/11* (2017.01); *G06T 7/13* (2017.01); *G06T 2207/10081* (2013.01); *G06T 2207/10116* (2013.01); *G06T 2207/20076* (2013.01); *G06T 2207/20081* (2013.01); *G06T 2207/20208* (2013.01); *G06T 2207/20224* (2013.01); *G06T 2207/30008* (2013.01); *G06T 2207/30048* (2013.01); *G06T 2207/30101* (2013.01); *G06T 2207/30204* (2013.01)

(56) References Cited

U.S. PATENT DOCUMENTS

| | | | | |
|---|---|---|---|---|
| 8,588,489 | B2* | 11/2013 | Pfister | A61B 6/487 |
| | | | | 382/128 |
| 8,639,009 | B2* | 1/2014 | Lang | A61B 6/505 |
| | | | | 382/132 |
| 9,642,586 | B2* | 5/2017 | Kelm | G06T 7/11 |
| 9,913,616 | B2* | 3/2018 | Fonte | A61B 6/50 |
| 10,007,983 | B2* | 6/2018 | Ohayon | A61B 8/0891 |
| 2004/0022359 | A1 | 2/2004 | Acharya et al. | |
| 2004/0081280 | A1 | 4/2004 | Avinash | |
| 2005/0173641 | A1 | 8/2005 | Unger et al. | |
| 2006/0120585 | A1 | 6/2006 | Zhang et al. | |
| 2007/0133736 | A1* | 6/2007 | Chen | A61B 6/00 |
| | | | | 378/5 |
| 2008/0226017 | A1 | 9/2008 | Altman et al. | |
| 2008/0232714 | A1 | 9/2008 | Nord et al. | |
| 2008/0304620 | A1 | 12/2008 | Karellas | |
| 2009/0279761 | A1 | 11/2009 | Fei et al. | |
| 2010/0156898 | A1* | 6/2010 | Voros | A61B 5/02007 |
| | | | | 345/419 |
| 2011/0081055 | A1 | 4/2011 | Bell et al. | |
| 2012/0027272 | A1* | 2/2012 | Akinyemi | G06T 7/11 |
| | | | | 382/128 |
| 2012/0121147 | A1 | 5/2012 | Huang et al. | |
| 2013/0094749 | A1 | 4/2013 | Oh et al. | |
| 2013/0108013 | A1* | 5/2013 | Leng | A61B 6/032 |
| | | | | 378/19 |
| 2014/0050378 | A1 | 2/2014 | Sengupta et al. | |
| 2014/0243579 | A1* | 8/2014 | Roeske | A61B 6/482 |
| | | | | 600/1 |
| 2015/0302578 | A1* | 10/2015 | Grady | G06T 7/0012 |
| | | | | 382/131 |
| 2017/0337343 | A1* | 11/2017 | Kakadiaris | G06F 19/00 |

FOREIGN PATENT DOCUMENTS

| | | |
|---|---|---|
| JP | 2008154718 A | 7/2008 |
| JP | 2010005252 A | 1/2010 |
| JP | 2012000297 A | 1/2012 |
| JP | 2014176515 A | 9/2014 |

OTHER PUBLICATIONS

Bentum, Mark J., et al. "Design and realization of high speed single exposure dual energy image processing." [1992] Proceedings Fifth Annual IEEE Symposium on Computer-Based Medical Systems. IEEE, 1992. (Year: 1992).*

Kappadath, S. Cheenu, and Chris C. Shaw. "Dual-energy digital mammography for calcification imaging: noise reduction techniques." Physics in Medicine & Biology 53.19 (2008): 5421. (Year: 2008).*

Sabol, John M., et al. "The impact of cardiac gating on the detection of coronary calcifications in dual-energy chest radiography: a phantom study." Medical Imaging 2006: Physics of Medical Imaging. vol. 6142. International Society for Optics and Photonics, 2006. (Year: 2006).*

Thielemans, Kris, Evren Asma, and Ravindra M. Manjeshwar. "Mass-preserving image registration using free-form deformation fields." 2009 IEEE Nuclear Science Symposium Conference Record (NSS/MIC). IEEE, 2009. (Year: 2009).*

Loeckx, Dirk, et al. "Temporal subtraction of thorax CR images using a statistical deformation model." IEEE Transactions on Medical Imaging 22.11 (2003): 1490-1504. (Year: 2003).*

Wen, Di, et al. "Coronary calcium visualization using dual energy chest radiography with sliding organ registration." Medical Imaging 2016: Image Processing. vol. 9784. International Society for Optics and Photonics, 2016. (Year: 2016).*

Schmermund, Axel, et al. "An algorithm for noninvasive identification of angiographic three-vessel and/or left main coronary artery disease in symptomatic patients on the basis of cardiac risk and electron-beam computed tomographic calcium scores." Journal of the American College of Cardiology (Year: 1999).*

Rocha-Filho, Jose A., et al. "Incremental value of adenosine-induced stress myocardial perfusion imaging with dual-source CT at cardiac CT angiography." Radiology 254.2 (2010): 410-419. (Year: 2010).*

Loog, M., van Ginneken, B., & Schilham, A. M. (2006). Filter learning: application to suppression of bony structures from chest radiographs. Medical image analysis, 10(6), 826-840. (Year: 2006).*

Zhuang, Xiahai, et al. "Multiatlas whole heart segmentation of CT data using conditional entropy for atlas ranking and selection." Medical physics 42.7 (2015): 3822-3833. (Year: 2015).*

Xu Tong, et al. "Fesibility of Real Time Dual-Energy Imaging Based on a Flat Panel Detector for Coronary Artery Calcium Quantification." Medical Physics, vol. 33, No. 6, May 10, 2006, pp. 1612-1622.

Sharma, et al. "Vascular Health and Risk Management Dovepress Cardiac Risk Stratification: Role of the Coronary Calcium Score." Vasuclar Health and Risk Management, Jan. 1, 2010, pp. 603-611.

Rasheed, et al. "Rib Suppression in Frontal Chest Radiographs: A Blind Source Separation Approach." IEEE International Symposium on Signal Processing and Its Applications, Feb. 12, 2007, pp. 1-4.

Wen, et al. "Coronary Calcium Visualization Using Dual Energy Chest Radiography with Sliding Organ Registration." Optical Sensing II, vol. 9784, Mar. 21, 2016.

Molloi, et al. "Quantification of Coronary Arterial Calcium by Dual Energy Digital Subtraction Fluoroscopy." Medical Physics, vol. 18, No. 2, Mar. 1, 1991 pp. 295-298.

(56) References Cited

OTHER PUBLICATIONS

International Search Report & Written Opinion of the International Searching Authority dated Jun. 24, 2016 for International Application No. PCT/US2016/027127.

* cited by examiner

DUAL ENERGY X-RAY CORONARY CALCIUM GRADING

CROSS REFERENCE TO RELATED APPLICATIONS

This Application is a Continuation of International Application number PCT/US2016/027127 filed on Apr. 12, 2016, which claims priority to U.S. Provisional Application No. 62/146,442 filed on Apr. 13, 2015. The contents of the above-referenced matters are hereby incorporated by reference in their entirety.

BACKGROUND

Coronary artery calcification (CAC) is a leading biomarker for predicting atherosclerotic heart disease. CAC is a more accurate predictor of cardiovascular risk than cholesterol and other lipids. CAC is also more accurate than C-reactive protein and carotid intima media thickness measured from ultrasound or magnetic resonance imaging (MRI) as a predictor of cardiovascular risk. CAC score reclassifies approximately 50% of intermediate-risk individuals to high or low risk categories, where there are established treatment strategies. Thus, CAC is a useful biomarker of cardiovascular disease and may be used to trigger drug therapy, lifestyle changes, or additional testing of cardiovascular health. Educating patients as to their risks related to atherosclerotic heart disease can improve adherence to drug therapies and lifestyle changes including smoking cessation, dietary changes, and weight loss. Adding a computed tomography (CT) coronary calcium score as a risk factor improves the ability to predict a cardiac event in a population of persons with no known cardiac disease. Showing patients their CT coronary calcium images and discussing CAC scores may improve adherence to statin drug therapy in high risk groups compared to treatment approaches without such an intervention.

In addition to screening, CAC scores derived from CT imaging may be used to determine next steps in therapy. The relative risk of obstructive angiographic coronary artery disease (CAD) is higher for coronary calcium scores (4.53) than either treadmill-electrocardiogram (ECG) (1.72) or technetium-stress (1.96). The accuracy of coronary calcium is also significantly higher (80%) than alternative approaches to predicting CAD in a patient, including treadmill testing (71%) and technetium-stress (74%). Thus, CAC scores derived from CT imaging have been used to guide a physician in determining what therapies to apply to a patient.

CT coronary calcium scoring is also used in the National Institute for Health and Care Excellence (NICE) practice guidelines as a gatekeeper in the CAD diagnostic pathway. Patients classified with a low likelihood of CAD with a modified Diamond-Forrester (DF) score in the range of 10% to 30% are scanned for CT coronary calcium. A zero calcium score rules out additional cardiovascular imaging, including non-invasive or invasive coronary angiograms. Additionally, CT coronary calcium scoring is a useful indicator for statin therapy. However, the high cost and high radiation dosage of CT imaging limits the utility of conventional CT-based CAC scoring as a screening tool for CAD.

BRIEF DESCRIPTION OF THE DRAWINGS

The accompanying drawings, which are incorporated in and constitute a part of the specification, illustrate various example apparatus, methods, and other example embodiments of various aspects of the invention. It will be appreciated that the illustrated element boundaries (e.g., boxes, groups of boxes, or other shapes) in the figures represent one example of the boundaries. One of ordinary skill in the art will appreciate that in some examples one element may be designed as multiple elements or that multiple elements may be designed as one element. In some examples, an element shown as an internal component of another element may be implemented as an external component and vice versa. Furthermore, elements may not be drawn to scale.

DETAILED DESCRIPTION

Figure 1:
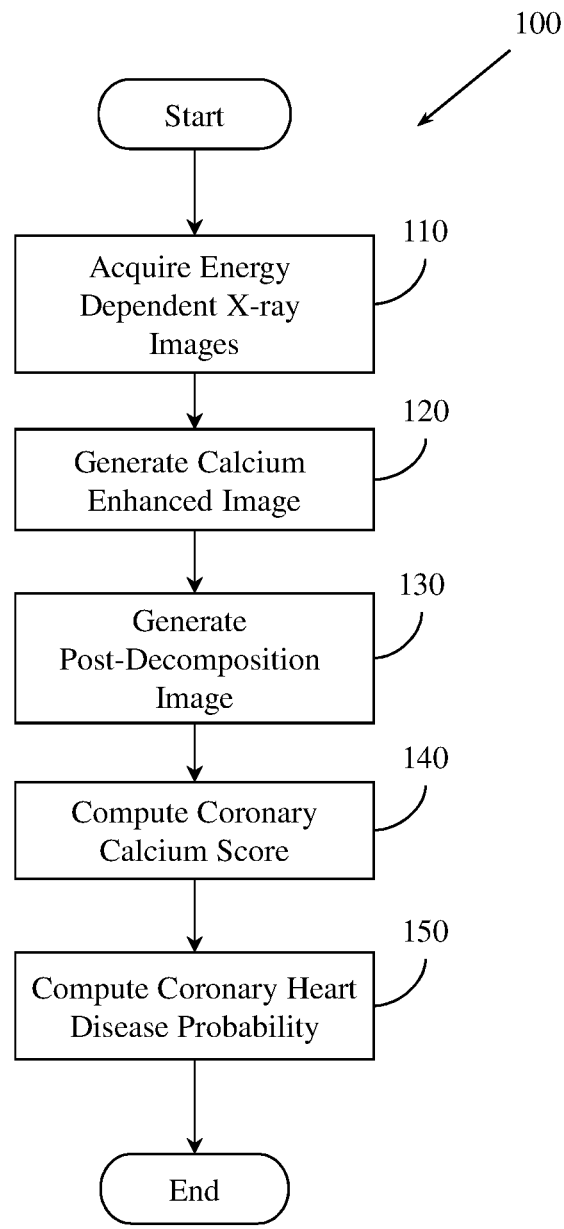
FIG. 1 illustrates an example method of predicting coronary heart disease.

Coronary artery calcification (CAC) is a leading biomarker for atherosclerotic heard disease. CAC has improved prognostic power compared to tests for lipids, C-reactive protein, and carotid intima media thickness when predicting coronary artery disease (CAD) events in asymptomatic patients. Additionally, CAC scores more accurately predict 15-year mortality in asymptomatic patients than non-CAC based approaches. Conventional approaches to CAC scoring employ computed tomography (CT) to obtain CAC imaging. However, conventional approaches that use CT involve relatively high costs and high radiation dosages, which limit the utility of conventional, CT-based approaches. Furthermore, CT imaging systems are physically large, immobile, and found most frequently in larger, well appointed hospitals.

Example methods and apparatus employ low cost, low radiation dual energy (DE) chest radiography to image CAC. Example methods and apparatus process DE chest radiography using anatomy aware registration or sliding organ registration to create a bone-image-like coronary calcium image (CCI) that reduces motion artifacts and improves CAC conspicuity compared to conventional approaches. Example methods and apparatus also suppress ribs in the DE chest radiography imagery to improve registration compared to conventional approaches.

Example methods and apparatus improve on conventional systems because CAC is a more accurate predictor of obstructive coronary artery disease than many conventional assessments of CAD risk, including lipid panels and blood pressure. Aortic valve calcium predicts aortic valve stenosis, a growing problem as the patient population ages. Aortic valve stenosis may be treated using minimally invasive procedures, including TAVR. Calcium deposits in other tissues, including the aorta and pulmonary arteries, are used by example methods and apparatus as biomarkers for general vascular disease. Example methods and apparatus improve on conventional systems by detecting and grading calcium deposits using a relatively inexpensive chest x-ray. Example methods and apparatus improve on conventional approaches, including CT-imagery based coronary calcium scores, because they are cheaper, faster, expose patients to a lower radiation dose, are less susceptible to motion artifacts, and offer improved accessibility compared to conventional approaches. By providing a cheaper, faster, and more accessible approach to grading CAC, example methods and apparatus may provide the quantifiable benefits of improving patient outcomes while reducing resource expenditure.

Example methods and apparatus create a coronary artery calcium image from DE chest x-ray images. Example methods and apparatus may also create pulmonary artery calcium, aorta calcium, and aortic valve calcium images from DE chest x-ray images Example methods and apparatus produce a coronary or valvular calcium image from low voltage (low kV) and high-voltage (high kV) chest x-ray images. Images may be acquired on a radiography system that takes low and high-voltage images in rapid succession. One radiography system with which example methods and apparatus may be implemented is General Electric's (GE) dual-energy digital radiography system with flat-panel technology. Other radiography systems may be employed.

Example methods and apparatus perform image processing to improve detection and grading of coronary calcium represented in the images. The image processing may include non-rigid registration, sliding organ registration, anatomy aware registration, rib suppression, selective filtering of low and high-energy images for calcium enhancement and noise removal, DE material decomposition to create a calcium image, and post enhancement processing. Generated output images can be viewed on various displays, including a picture archiving and communication (PACS) system. Example methods and apparatus detect CAC and generate a CAC grade using features detected in the images. CAC detection and grading of images is performed using features proven from clinical studies comparing processed dual energy images to corresponding CT calcium scores. Example methods and apparatus compute a coronary calcium score based, at least in part, on the output image, and compute a coronary heart disease probability based, at least in part, on the coronary calcium score. In one embodiment, example methods and apparatus automatically analyze the images and provide a quantitative calcium score. The quantitative calcium score may be based, at least in part, on the detected features or CAC grade. The quantitative calcium score may be used to generate a probability that a patient will experience CAD.

Example methods and apparatus use dual energy x-ray to decompose soft-tissue images and bone images from high kV and low kV projection x-ray images. The high kV image and the low kV image are used to decompose the anatomy represented in the images and to create soft tissue images and bone images of the desired anatomical region. The high kV image and the low kV image are decomposed according to the DE decomposition equation:

$$I_B = I_L^{W_B}/I_H \qquad (1)$$

where $I_B$ is the bone image, $I_L$ is the low kV image, $I_H$ is the high kV image, and $W_B$ is the decomposition coefficient.

By acquiring two image exposures at different energy levels, the DE digital radiography contains redundant information. The redundant information is used to decompose calcified anatomy from the posterior anterior (PA) view, thus providing a better view of observing heart related calcification than that provided by plain chest film.

Conventional DE radiography systems have low sensitivity and low specificity for heart related calcification diagnosis. Conventional approaches are sub-optimal in clinical situations because they suffer from motion artifacts derived from different acquisition times, and motion artifacts caused by heart motion. Conventional approaches are also sub-optimal because they may capture non-cardiac anatomic background, including spine, ribs, lung artery, and vessels. Conventional approaches are also exposure control optimized for lung imagery, which is not ideal when imaging coronary calcium. In conventional approaches, the heart anatomy may thus be under-exposed or obscured. Example methods and apparatus improve on conventional approaches by eliminating or mitigating these problems through the application of CAC optimized registration techniques.

In DE x-ray imaging, x-ray projection images are acquired in an energy-dependent manner. Example methods and apparatus may employ multiple approaches for acquiring x-ray projection images in an energy-dependent manner. The multiple approaches may include switching kV between and high and low values to create high and low x-ray spectra, switching kV and mA to create high and low x-ray spectra, switching pre-filtration x-ray filters to create high and low x-ray spectra, or switching pre-filtration x-ray filters and kV to create high and low x-ray spectra. The multiple approaches may also include using a sandwich detector where low and high energy x-rays are detected in the first detector and second detector, respectively, or using photon counting, energy sensitive detectors.

One embodiment employs switching kV between and high and low values, creating high and low x-ray spectra. The detector may be a digital detector with fast offloading of images from the detector, such as an x-ray flat panel detector. Example methods and apparatus may employ X-ray exposure times of less than 15 ms to limit motion blur in a single image. When switching is used, the timing of switching may be controlled by electrocardiograph (EKG) triggering. When EKG triggering is not used, the time between acquisitions may be less than 150 ms. If EKG triggering is used and images are acquired on subsequent heartbeats, the time between acquisitions may be approximately 1 s, with delay computed from the R wave. If there is EKG triggering and images are to be acquired during the same heartbeat, the time between acquisitions may be less than 100 ms, delayed an appropriate time from the R wave.

Example methods and apparatus may employ a heart related calcification decomposition entity. The inputs of the heart related calcification decomposition entity are the original low kV and high kV images. A bone/calcium enhancing image is output by the heart related calcification decomposition entity to an image displaying entity. The bone/calcium enhancing image is computed through a pre-decomposition process, a selective filtering process, and a dual-energy subtraction process.

An original low kV image $I_L$ and high kV image $I_H$ may be processed by the pre-decomposition process before being input to the selective filtering process and the dual-energy subtraction process. The pre-decomposition process minimizes motion artifacts captured in the low kV image $I_L$ and high kV image $I_H$ due to heart beats and respiratory motion that occurred in the patient being imaged during dual-energy chest radiography.

In one embodiment, the input low kV image $I_L$ and high kV image $I_H$ are normalized to generate a normalized low kV image $I_L^1$ and a corrected high kV image $I_H^1$. The normalization process may also include a scatter estimation process for $I_L$ and $I_H$ to obtain scatter parameters $I_{L4}=I_{L3}-sc_{low}$ and $I_{H4}=I_{H3}-sc_{high}$, which may be used in equations (10) and (11) described herein.

CAC contrast may be degraded by motion artifacts, Compton scattering, beam hardening, or quantum noise. Example methods and apparatus may compute an estimated scatter image from an exposure using convolution filtering. The estimated scatter image may be subtracted from the original raw image before registration and before DE decomposition. Example methods and apparatus reduce quantum noise in CCI by applying Gaussian blurring low pass filters to the low kV image or to the high kV image before DE decomposition.

Example methods and apparatus improve registration accuracy compared to conventional approaches by performing heart silhouette segmentation. A heart silhouette $I_c$ is segmented out from the low kV image and the high kV image as a binary mask to constrain the registration process. Example methods and apparatus preserve motion discontinuity across the heart contour using the binary mask. Preserving motion discontinuity across the heart contour facilitates detecting severe heart contour motion. In one embodiment, heart silhouette segmentation is performed using dynamic programming. An initial heart silhouette $I_c^{(0)}$ is computed in the low kV image. The low kV image has a higher heart-to-lung contrast than the high kV image. $I_c^{(0)}$ is then enlarged to $I_c$ so that $I_c^{(0)}$ covers the deformed heart silhouette in the high kV image. Example methods and apparatus may dilate $I_c^{(0)}$ with a margin d. The margin d may be user-adjustable within a threshold range. $I_c$ may then be used as an input to the registration process. For example, $I_c$ may be used in sliding registration.

Example methods and apparatus perform registration between the low energy x-ray image and the high energy x-ray image using a reference image and a floating image. The low energy x-ray image is the reference image, and the high energy x-ray image is the floating image. In one embodiment, $I_L^1$ is the reference image $I_r$ and $I_H^1$ is the floating image $I_f$.

Example methods and apparatus may employ a parametric motion model when registering images. A parametric motion model T: $\vec{x} \rightarrow \vec{x}'$ is defined to transform the coordinates $\vec{x}$ of a floating image (e.g. $I_H^1$, $I_f$) voxel to its corresponding coordinates $\vec{x}'$ in the reference image (e.g. $I_L^1$, $I_r$) coordinate system. Alternatively, the motion model T: $\vec{x} \rightarrow \vec{x}'$ may be characterized by a deformation field $V(\vec{x})$ defined on a floating image grid, which can be computed from T or other specified functions, so that $\vec{x}'=\vec{x}+V(\vec{x})$.

For rigid registration, T is a 3-by-3 matrix defined below as equation (2):

$$\vec{x}' = T(\vec{x}) = T\left(\begin{bmatrix} x \\ y \\ 1 \end{bmatrix}\right) = \begin{bmatrix} \theta_{11} & \theta_{12} & \theta_{13} \\ \theta_{21} & \theta_{22} & \theta_{23} \\ 0 & 0 & 1 \end{bmatrix}\begin{bmatrix} x \\ y \\ 1 \end{bmatrix}. \quad (2)$$

For piece-wise registration, the floating image $I_f$ is divided into non-overlapping sub-images: $I_f = I_f^{(1)} \cup I_f^{(2)} \cup \ldots \cup I_f^{(M)}$, so that a sub-image $I_f^{(m)}$ is associated with an affine transformation model $T^{(m)}$ as defined in equation (2).

For perspective registration, T is a defined as the following perspective projection function (3):

$$\vec{x}' = T(\vec{x}) = T\left(\begin{bmatrix} x \\ y \\ 1 \end{bmatrix}\right) = \frac{\begin{bmatrix} \theta_{11} & \theta_{12} & \theta_{13} \\ \theta_{21} & \theta_{22} & \theta_{23} \\ 0 & 0 & 1 \end{bmatrix}\begin{bmatrix} x \\ y \\ 1 \end{bmatrix}}{\begin{bmatrix} \theta_{31} & \theta_{32} & 1 \end{bmatrix}\begin{bmatrix} x \\ y \\ 1 \end{bmatrix}}. \quad (3)$$

For non-rigid registration, a non-linear motion model is characterized through the definition of a deformation field. The deformation field $V(\vec{x})$ can be computed by the following non-linear parameterized spline based function:

$$V(\vec{x})=V(x,y)=\Sigma_{l=0}^{Q}\Sigma_{m=0}^{Q} B_l(u)B_m(v)\phi_{l+i,m+j} \quad (4)$$

where $i=\lfloor x/n_x \rfloor$, $j=\lfloor y/n_y \rfloor$, $u=x/n_x-i$, $v=y/n_y-j$, Q is the number of B-spline basis functions, $B_l$ represents the lth basis function of the B-spline, and $\Phi_{REG}=\{\phi_{i,j}|i=1\sim M, j=1\sim N\}$ is the pre-defined mesh of control points determining the shape of $V(\vec{x})$. When a B-spline basis function is a cubic B-Spline, Q=3. Therefore, the number of parameters in the non-rigid motion model is determined by the number of control points M×N where $$M = \left\lfloor \frac{M_x}{n_x} \right\rfloor \text{ and } = \left\lfloor \frac{M_y}{n_y} \right\rfloor.$$

In one embodiment, a radial basis function (RBF) may be employed to define $V(\vec{x})$. In another embodiment, other functions may be used to define $V(\vec{x})$.

In one embodiment, a warping result $T(I_f)$ of the floating image $I_f$ is computed based on the parametric motion model T. The image grid coordinates $\vec{x}$ of $I_f$ are transformed to the corresponding coordinates $\vec{x}'$ in the reference coordinate system using the motion model T or the deformation field $V(\vec{x})$. The voxel values of the transformed floating image are interpolated at the reference image grid by the nearby transformed floating image voxel values using bilinear or bicubic interpolation. In another embodiment, other types of interpolation may be used.

Example methods and apparatus may be optimized. The optimization may be based on the motion model T or the deformation field $V(\vec{x})$. Based on the type of motion model employed by an embodiment, an objective function value can be computed as:

$$\mathcal{C}(I_r,I_f,T)=-\mathcal{C}_{sim}(I_r,T(I_f))+\lambda \cdot \mathcal{R}(T) \quad (5)$$

where $\mathcal{C}_{sim}(\cdot)$ is a similarity measurement of two images and $\mathcal{R}(\cdot)$ is a regularization term to penalize unreasonable motion model parameters. The two images may include the reference image and the floating image.

Example methods and apparatus may employ a first similarity function for $\mathcal{C}_{sim}(\cdot)$, or a second, different similarity function for $\mathcal{C}_{sim}(\cdot)$. The similarity function may be selected by a user. Example methods and apparatus may use a first regularization function for $\mathcal{R}(\cdot)$, or a second, different regularization function. The regularization function may be selected by a user.

Example methods and apparatus choose a set of optimal parameters of the motion model T to match the reference image and the floating image. In one embodiment, a gradient descending based algorithm is used to search for the set of optimal parameters. The gradient descending based algorithm facilitates the minimization of the objective function value $\mathcal{C}$:

$$T^* = \operatorname{argmin}_T \mathcal{C}(I_r, I_f, T) \qquad (6).$$

In one embodiment, example methods and apparatus may use anatomy-aware registration to register the high kV image with the low kV image. Anatomy aware registration employs knowledge of heart anatomy for heart registration. The deformation field $V(\vec{x})$ is interpolated from deformation vectors estimated at a set of sparse key-points. Example methods and apparatus define a set X of key-points $X = \{(x_i, y_i) | i=1 \sim K\}$ characterizing common anatomical landmarks of different heart images. Example methods and apparatus may use a manual annotation of X on a set of training chest x-ray images to compute a model $M_{Heart}$ describing the shape of the heart anatomy. In one embodiment, X may be annotated automatically.

Example methods and apparatus detect the corresponding locations of X in an image using the model $M_{Heart}$. Example methods and apparatus may detect the corresponding locations of X using an iterative technique. The detection process is conducted on the high kV image and the low kV image to obtain the key-points $X_L$ in the low kV image and $X_H$ in the high kV image. The deformation vectors at the corresponding key-points, $\Delta X = X_H - X_L = \{(x_i^H - x_i^L, y_i^H - y_i^L) | i=1 \sim K\}$, are used to interpolate the deformation field $V(\vec{x})$. For example, $V(\vec{x})$ is defined using B-spline interpolation in equation (4) and subjected to the constraint that $V(x_i, y_i) = (x_i^H - x_i^L, y_i^H - y_i^L)$. Optimization of $V(\vec{x})$ is performed by minimizing the objective function represented in equation (5) with an additional constraint at the landmarks.

In one embodiment, example methods and apparatus may employ sliding registration to register the low kV image and the high kV image. In DE chest radiography of patients with CAC, both the low kV exposure and the high kV exposure contain CAC signals, but with different contrasts levels relative to the background. For example, the low kV image may have larger CAC contrast and better CAC image quality than the high kV image. Example methods and apparatus use the low kV image as the reference image and the high kV image as the floating image. Thus, even though the high kV image may be deformed before DE subtraction, the low kV image will be intact, thereby preserving the major CAC appearance in the final CCI.

A significant proportion of motion artifacts in the CCI concentrate in the vicinity of the heart contour. Example methods and apparatus use the heart silhouette $I_c$ as a binary mask to constrain the registration process to focus on the alignment of the heart contour. For regions inside the heart silhouette $I_c$, example methods and apparatus use a free form deformation (FFD) model to parameterize a motion field $T(\vec{x})(\vec{x} = (x,y))$ between two images. For two dimensional (2D) image registration on an X×Y plane, the FFD model constructs $T(\vec{x})$ by interpolating a series of B-spline basis functions with a mesh of uniform spacing control points $$\Phi = \left\{ \phi_{i,j} \mid 0 \le i \le \left\lfloor \frac{X}{\delta} \right\rfloor, 0 \le j \le \left\lfloor \frac{Y}{\delta} \right\rfloor \right\},$$

where $\delta$ is the uniform space between adjacent control points, as:

$$T(\vec{x}) = T_\Phi(\vec{x}) = \sum_{m=0}^{3} \sum_{n=0}^{3} B_{m,n}(\vec{u}) \phi_{i+m, j+n}$$

where $B_{m,n}$ is the tensor product of the mth and nth ($0 \le m, n \le 3$) one dimensional (1D) cubic B-spline functions.

Upon defining the motion field, the registration process finds optimal motion values at control point mesh grids such that example methods and apparatus minimize a first cost function described by:

$$C(\Phi) = -C_{similarity}(I_0, T_\Phi(I_1)) + \lambda C_{smooth}(\Phi)$$

where $I_0$ is the reference image and $I_1$ is the floating image.

In conventional approaches that use FFD, the first cost function is calculated throughout the whole image. Thus, in conventional approaches, motion outside the heart contributes to the cost function and also affects the adjustment of grid points inside the heart. Conventional approaches thus suffer from severe registration error along the heart contour, since the deformation smoothness constraint prohibits large motion discontinuity across the heart contour. Example methods and apparatus improve on conventional approaches by adding a mask to the FFD registration cost function:

$$C(\Phi, I_C) = -C_{similarity}(I_0 \cap I_C, T_\Phi(I_1) \cap I_C) + \lambda C_{smooth}(\Phi)$$

where $I \cap I_C$ denotes the operation to extract a pixel subset from image I where pixel values in the binary mask or silhouette $I_C$ equal 1.

Changing the value at any control grid $\phi_{i,j}$ outside the mask $I_C$ has no effect on the mutual information term $C_{similarity}(*)$. Thus, example methods and apparatus improve on conventional approaches because motion estimation outside the mask has no effect on the registration process inside the mask, and registration inside the heart mask is improved. To stitch a complete chest image for clinical output, example methods and apparatus may further register the low kV image and the high kV image outside the heart silhouette $I_C$ (i.e., within the complementary mask $\overline{I_C}$), using a rigid deformation model. Upon estimating motion parameters inside and outside the heart silhouette, example methods and apparatus transform the inside and outside parts of the high kV image, and stitch the inside and outside parts of the high kV image into a complete image using soft weighting.

During optimization, a series of constraints may be applied to specific regions in the floating image $I_f$ to further limit the searching range of the motion model parameters in these regions. For example, in non-rigid registration, including sliding registration, a bi-level mask covering the heart may be extracted to constrain the optimization process so that non-rigid deformation is only allowed inside the mask (e.g., the heart). After the pre-decomposition process, the low energy image and the transformed high energy image are output for the next process.

Example methods and apparatus improve registration accuracy compared to conventional approaches by using layer separation pre-processing. Layer separation pre-processing includes separating bone layers in $I_L$ and $I_H$ and suppressing bone layers in $I_L$ and $I_H$ before registration.

Layer separation pre-processing may use rib suppression. Rib suppression may be employed along with registration techniques, including sliding organ registration or anatomy-aware registration techniques.

To generate a rib suppressed image, example methods and apparatus compute an initial bone image $B$ in the cardiac region without registration. The initial bone image $B$ has four posterior rib pairs. Example methods and apparatus compute a rib edge map $B_1$ from $B$. The rib edge map $B_1$ displays the probability of rib edge occurrence at a pixel within the image. The edge map $B_1$ may be calculated using simple edge filters or using a convolutional neural network trained from rib-annotated images with a supervised learning process. The rib-annotated images may be manually annotated, or may be automatically annotated.

Example methods and apparatus generate a binary segmentation rib mask $B_{Mask}$ from the edge map $B_1$. In one embodiment, the binary segmentation rib mask $B_{Mask}$ is generated by integrating the rib edge map intensity and a prior rib shape model $M_B$. The rib shape model $M_B = \{\rho_B, \delta_B\}$ contains a single rib model $\rho_B$ and an inter-rib model $\delta_B$. The single rib model $\rho_B$ includes four corner points and quadric curves between the four corner points. The single rib model $\rho_B$ is used to approximate a rib contour instantiation using multi-variate Gaussian distribution of the corner coordinates. The inter-rib model $\delta_B$ characterizes the inter-relationship of adjoining ribs by multi-variate Gaussian distribution of their corner point offset. In one embodiment, the segmentation process is similar to inferring the Maximum A Posteriori (MAP) rib locations $\theta_B$ by considering both the rib likelihood and a geometric shape prior: $\theta_B^* = \text{argmax}_{\theta_B} (\mathcal{L}(\theta_B, B_1) - \mathcal{E}(\theta_B, M_B))$, where $\mathcal{L}(\theta_B, B_1)$ is the likelihood of a rib contour. The likelihood of a rib contour $\mathcal{L}(\theta_B, B_1)$ can be calculated by the inner product between contour $\theta_B$ and corresponding pixel values in the rib edge map $B_1$. In one embodiment, the geometric shape prior may be defined as a penalty term proportional to the Euclidean distance between rib contour $\theta_B$ and the nearest plausible rib shape generated by model $M_B$. Example methods and apparatus may use a particle filter based technique to generate the binary segmentation rib mask $B_{Mask}$. In one embodiment, the center locations of the sixth rib and the seventh rib in the chest (in the upper-right portion of the cardiac region) are initialized. A set of particles $\Theta = \{\theta_B^i | i=1 \sim T\}$ is created which sample T rib instantiations around the initial location following a multi-variate Gaussian distribution. Example methods and apparatus calculate the likelihood of each particle: $\mathcal{L}(\theta_B^i, B_1)$. The MAP estimation of the rib location is obtained by calculating the mean location of members of the set of particles weighted by their likelihood: $\theta_B^* = \Sigma \mathcal{L}(\theta_B^i, B_1) \cdot \theta_B^i / \Sigma \mathcal{L}(\theta_B^i, B_1)$. In one embodiment, this process proceeds from right to left, and top to bottom to catch the other ribs sequentially. In another embodiment, the center locations may be initialized on ribs other than the sixth rib and the seventh rib. In another embodiment, this process may proceed from left to right, or from bottom to top.

Example methods and apparatus separate the rib signal inside the mask using the rib mask $B_{Mask}$ and independent component analysis (ICA). Rib signals in $I_L$ and $I_H$ are estimated and the rib signals are subtracted from $I_L$ and $I_H$ to create rib suppressed images for further processing.

Example methods and apparatus may employ selective filtering. After pre-decomposition, the low energy image $I_L^2$ and the transformed high energy image $I_H^2$ may be convolved by selective filters before the dual-energy subtraction process. By employing selective filtering, example methods and apparatus eliminate noise and enhance coronary artery calcification contrast in the decomposition process.

Example methods and apparatus may filter the low energy image and the high energy image. For the low energy image $I_L^2$, a Gaussian filter $G_{\sigma_x, \sigma_y}(x,y)$, where $\sigma_x = \sigma_y = s$, is applied to remove quantum noise and preserve the vessel-like structures in $I_L^2$.

For the high energy image $I_H^2$, the vessel-like excursions are wiped off or removed from the image using a fine tuned filter F. In one embodiment, F can be a vesselness measure operator followed by a morphological suppression process. In one embodiment, F may include computing a vesselness map $I_v$ from $I_H^2$, computing a group of connected regions C with high vesselness responses in $I_v$, or applying Gaussian filtering or gray-scale morphological operations to smooth pixel intensities in C.

Another embodiment may employ an implementation of F that includes a directional low pass filter with a specific direction parameter $\theta_d$ and a width parameter $W_d$. The directional low pass filter may be tuned to suppress structures in $I_H^2$ with orientation close to $\theta_d$ and spatial width less than $W_d$.

The implementation of the directional low pass filter includes constructing a directional band-pass filter bank. The band-pass filter bank may include forms of directional band-pass filters with a directional parameter $\theta$ and a width parameter W. Example methods and apparatus may use the steerable filter:

$$F_{\theta,W}(x,y) = \mathcal{R}^\theta (F_{0,W}(x,y)) \quad (7)$$

where $F_{0,W}(x,y)$ is the filter function oriented at $\theta = 0$, and $\mathcal{R}^\theta(\cdot)$ is the operation to rotate $F_{0,W}(x,y)$ to an arbitrary angle $\theta$.

$F_{0,W}(x,y)$ is computed as a derivative of a basic function, which may be a 2D isotropic function. For example, one embodiment may use the 2D Gaussian function as the basic function and compute $F_{0,W}(x,y)$ as the first derivative of the Gaussian function:

$$F_{0,W}(x,y) = \frac{\partial}{\partial x} G_{W,W}(x,y). \quad (8)$$

Another example embodiment may use the second derivative of the 2D Gaussian function:

$$F_{0,W}(x,y) = \frac{\partial^2}{\partial x^2} G_{W,W}(x,y). \quad (9)$$

Example methods and apparatus may construct a dedicated filter bank $\mathcal{F} = \{F_{\theta_i, W_j}(x,y) | i=1 \sim N, j=1 \sim K\}$ to capture image content at different directions and widths, where N is the number of orientations and K is the number of scales. In one embodiment, the directional filtering process is accomplished by convolving $I_H^2$ with a bank of directional band-pass filters $\mathcal{F}$, producing a vector of filter responses, and multiplying filter responses in channels by a weighting coefficient, where the weighting coefficient is set to amplify or suppress the selective direction and width corresponding to the current channel. The directional filtering process is further accomplished by applying the transformed filter response vector to the image re-construction process to output the directional low-pass filtered image.

The parameter set of the selective filtering process is defined as: $\Phi_{SF}=\{s,\theta_d,W_d\}$.

Example methods and apparatus may employ a DE subtraction process. After the selective filtering process, the filtered low energy image $I_L^3$ and high energy image $I_H^3$ are output to the DE subtraction process for material decomposition. Material decomposition eliminates soft-tissue anatomic structures that may distract from the diagnosis of coronary artery calcification.

In one embodiment, $I_L^3$ and $I_H^3$ are corrected for scatter removal using the following equations $$I_L^4=I_L^3-sc_{low} \quad (10)$$

and $$I_H^4=I_H^3-sc_{high} \quad (11).$$

The bone image $I_{B1}$ is computed by the following equation:

$$I_{B1}=I_L^{4WB}/I_H^4 \quad (12).$$

The parameter set of the dual-energy subtraction process is defined as $\Phi_{DES}=\{sc_{low}, sc_{high},W_B\}$.

Example methods and apparatus may employ a post-decomposition process to further amplify heart related calcification and eliminate calcium anatomic structures inside the heart but not relevant to coronary artery calcification. In one embodiment, an un-sharp mask enhancement process may be performed on $I_{B1}$:

$$I_{B2}=I_{B1}-w_E \times \text{LPF}(I_{B1}) \quad (13)$$

where $w_E$ is the un-sharp coefficient within the range [0,1] and LPF(·) is the low-pass filtering operation.

The low-pass filtering operation LPF(·) is defined as:

$$\text{LPF}(I)=G_{\sigma_E,\sigma_E}(x,y) \otimes I \quad (14)$$

where ⊙ represents the convolution operation.

Another embodiment may employ post-decomposition. Post-decomposition may include a spine/rib removal process. The spine/rib removal process estimates a spine/rib background image $I_{SR}$ and subtracts it from $I_{B1}$.

Example methods and apparatus may apply a dynamic range adjustment to $I_{B2}$, to produce a final output $I_{B3}$. Adjusting the dynamic range of $I_{B2}$ may bring the dynamic range of $I_{B3}$ to within an appropriate dynamic range $[R_{min}, R_{max}]$ that matches parameters associated with the dynamic range of a target displaying device or a storage format. Adjusting the dynamic range thus facilitates displaying CAC images generated by example methods and apparatus on a variety of display types, and storing them on a variety of storage devices.

The parameter set of the post-decomposition process is defined as: $\Phi_{POST}=\{w_E,\sigma_E,R_{min},R_{max}\}$.

In one embodiment, the calcification decomposed image is displayed independently, or together with other image exposures, including a standard PA chest radiography image, an oblique view, or CT results, for heart related calcification diagnosis. The calcification decomposed image may be displayed on a desktop computer, a laptop computer, a tablet computer, a personal electronic device (PED), a smart phone, or other device capable of displaying a calcification decomposed image.

Example methods and apparatus produce the concrete, real-world technical effect of increasing the probability that at-risk patients receive timely treatment tailored to the particular pathology presented. The additional technical effect of reducing the expenditure of resources and time on patients who are less likely to suffer recurrence or disease progression is also achieved. Example methods and apparatus thus improve on conventional approaches in a measurable, clinically significant way.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic, a circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

FIG. 1 illustrates an example method 100 of predicting coronary heart disease. Method 100 includes, at 110, acquiring a set of energy dependent images of a region of tissue. Acquiring the set of energy dependent images may include, for example, receiving a file from a radiographic system, including an x-ray imaging system, reading a value from a computer memory, reading a value from a data storage device (e.g., disk, tape, solid state device (SSD)), receiving a value from the cloud, or other computer based activity. The set of energy dependent images includes a first energy x-ray image and a second, different energy x-ray image. In one embodiment, first energy x-ray image is a 60 kV exposure and the second, different energy x-ray image is a 120 kV exposure. In this embodiment, the first energy x-ray image and the second, different energy x-ray image are acquired within a 150 ms interval.

In one embodiment, acquiring the set of energy dependent images includes creating a high x-ray spectrum and a low x-ray spectrum by switching kV between a first, high kV value, and a second, lower kV value. In this embodiment, the first, high kV value is 120 kV, and the second, lower kV value is 60 kV. In another embodiment, acquiring the set of energy dependent images includes creating a high x-ray spectrum and a low x-ray spectrum by switching kV and mA, by switching pre-filtration x-ray filters, or by switching pre-filtration x-ray filters and kV.

In one embodiment, the set of energy dependent images is acquired using a photon counting, energy sensitive detector. The set of energy dependent images may also be acquired by using a sandwich detector that includes a first detector and a second different detector. In this embodiment, the first energy x-ray image is acquired using the first detector, and the second energy x-ray image is acquired using the second detector. In other embodiments, other types of detectors, or other kV values may be used.

In one embodiment, method 100 acquires the set of energy dependent images using EKG triggering to control the timing of the switching. The EKG triggering may be based upon a percentage of a running average of R-R wave intervals associated with the patient being imaged. In another embodiment, the EKG triggering may be based on other properties of the patient being imaged or of the x-ray imaging system used for acquiring the set of energy dependent images.

Example methods and apparatus may employ a specialized EKG gated dual energy x-ray imaging system for detection and grading of coronary calcium. Example methods and apparatus employing a specialized EKG gated dual energy x-ray imaging system improve on conventional approaches by being easier to use and giving more accurate results than the conventional state of the art chest imaging systems without EKG triggering.

In one embodiment, a patient may sit in a chair or lie on a table with rests aiding arm extension. Source and detector allow rapid pre-programmed positions suitable for viewing major coronary territories, including the right coronary artery (RCA), left anterior descending (LAD) artery, left circumflex (LCX), or left main (LM) coronary artery. At least two oblique views are used to acquire the set of energy dependent images. One embodiment includes a c-arm.

One embodiment uses a single-lead EKG system having two electrode contacts to skin on two hands or limbs of the patient being imaged to perform EKG acquisition. A gel pad is applied to the palms of a patient's hands. R waves from the patient are detected, R-R intervals are recorded, and a quality metric ensures that R-R intervals are accurate. Triggering is based upon a percentage of a running average of R-R intervals. The running average of R-R intervals may be, for example, 40%. Other percentages may be used by other embodiments. Triggering occurs upon detection of a patient heart beat following initiation by an operator. If an R wave is not detected within a tolerance threshold, a misfire is recorded and the operator is instructed to check the leads and begin the process again.

Example methods and apparatus may trigger acquisition of the high kV image and the low kV image within one R-R interval. An optimal delay for reduced coronary motion is approximately 40-50% of the R-R interval with a dependence based upon a detected heart rate. An optimal spot may be found if the total acquisition time is 30-50 ms for the dual acquisition. Example methods and apparatus may employ end systolic acquisition. An advantage of an end systolic acquisition is that the heart filling will be minimized, yielding reduced degradation effects, including reduced attenuation, beam hardening, or scatter, compared to conventional approaches.

Example methods and apparatus may use a flat panel x-ray detector with a digital store allowing images to be acquired in rapid succession. Conventional approaches may acquire images at an interval of 150 ms for a panel of two thousand by two thousand pixels, where a significant portion of the 150 ms is the read time of the panel. One embodiment of example methods and apparatus described herein uses a smaller field of view than conventional approaches, providing a panel of approximately one thousand by one thousand pixels at the same resolution as conventional approaches. In this embodiment, the number of pixels is one million as compared to five million in the conventional approach, and this reduces the read time of example methods and apparatus by at least 25% compared to conventional approaches. Example methods and apparatus thus facilitate reducing the time between acquisitions to, for example, 40 ms. This embodiment reduces motion significantly compared to conventional approaches. When a vessel velocity of 30 mm/s is used, example methods and apparatus result in a motion of only 1.2 mm. This is a substantial improvement to the conventional motions of 4.5 mm at 30 mm/s or 9 mm at the maximum velocity of approximately 60 mm/s that are achieved by ungated conventional approaches. By using a smaller field of view, example methods and apparatus thus improve on conventional approaches because scatter is reduced, and acquisition time is reduced.

Method 100 also includes, at 120, generating a calcium-enhanced image of the region of tissue. Generating the calcium-enhanced image includes generating a set of pre-decomposition images by pre-decomposition processing the set of energy dependent images. Pre-decomposition processing may include normalizing the set of energy dependent images, or registering the set of energy dependent images. Generating the calcium-enhanced image also includes generating a set of selectively filtered images by selectively filtering the set of pre-decomposition images. Generating the calcium enhanced image also includes generating a set of dual energy subtraction images by dual energy decomposing the set of selectively filtered images.

Method 100 also includes, at 130, generating a post-decomposition image. The post-decomposition image is based, at least in part, on the calcium enhanced image. In one embodiment, generating the post-decomposition image includes applying un-sharp masking to the set of dual energy subtraction images. The un-sharp masking is based on the set of dual energy subtraction images, an un-sharp coefficient, and low-pass filtering operation. In one embodiment, the value of the un-sharp co-efficient is within the range [0, 1). In another embodiment, the value of the un-sharp co-efficient may be within another, different range.

Method 100 also includes, at 140, computing a coronary calcium score. Method 100 computes the coronary calcium score based, at least in part, on the post-decomposition image. In one embodiment, computing the coronary calcium score includes extracting a set of features from the post-decomposition image. Computing the coronary calcium score also includes relating the set of features to a set of vessel-territory specific CT calcium scores. The coronary calcium score is based, at least in part, on the relation of the set of features to the set of vessel-territory specific CT calcium scores. In one embodiment, a support vector machine (SVM) is trained on the set of vessel-territory specific CT calcium scores. Method 100 relates the set of features to the set of vessel-territory specific CT calcium scores using SVM regression. The set of features may include an exposure time feature, a vesselness filtering feature, a texture feature, a shape feature, or a curvedness feature. In another embodiment, the set of features may include other, different features.

Method 100 also includes, at 150, computing a coronary heart disease probability. The coronary heart disease probability is based, at least in part, on the coronary calcium score. In one embodiment, method 150 controls a computer aided diagnosis (CADx) system to compute the coronary heart disease probability.

Figure 4:
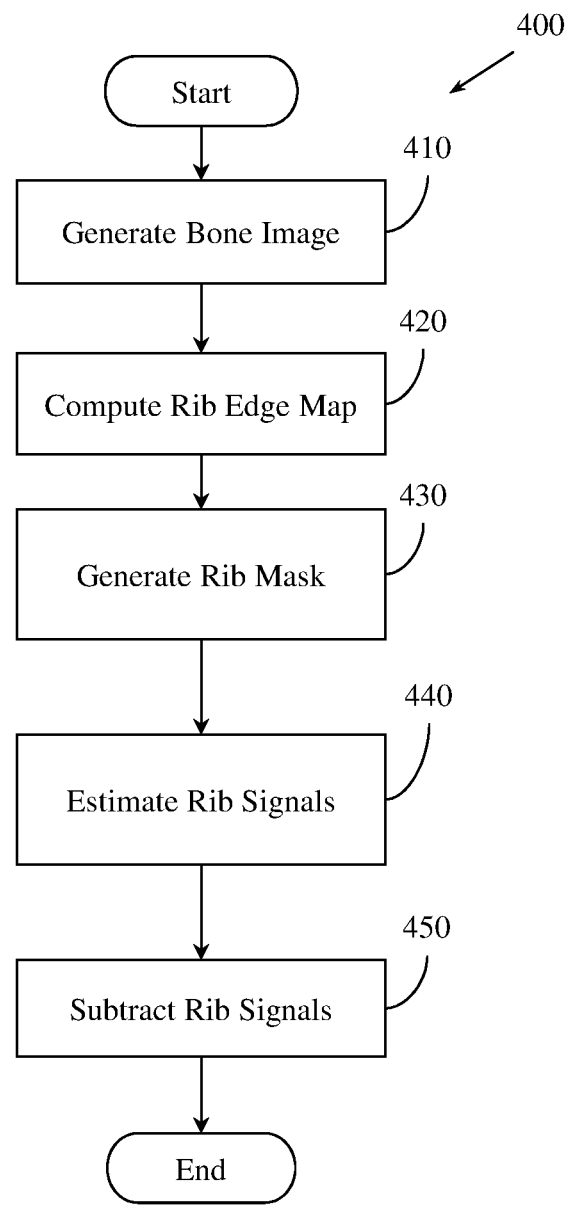
FIG. 4 illustrates an example method for generating a rib suppressed image.

In one embodiment, method 100 further comprises generating a set of rib suppressed images. The set of rib suppressed images may be based on the set of energy dependent images. FIG. 4 illustrates an example method 400 of generating a set of rib suppressed images that may be implemented by example methods and apparatus described herein. Method 400 includes, at 410, generating a bone image of the region of tissue. The bone image is based on the set of energy dependent images. The bone image includes a plurality of pixels.

Method 400 also includes, at 420, computing a rib edge map. In one embodiment the rib edge map is computed using an edge filter. In another embodiment, the rib edge map is computed using a convolutional neural network. The convolutional neural network is trained on a set of rib-annotated images. The set of rib-annotated images may be annotated by an expert pathologist, or may be annotated automatically. The convolutional neural network may be trained using a supervised machine learning process. The rib edge map displays a probability of rib edge occurrence at a pixel within the bone images. The rib edge map has a continuous intensity. The continuous intensity may be between 0 and 1. In another embodiment, the continuous intensity may be within a different range.

Method 400 also includes, at 430, generating a binary segmentation rib mask. The binary segmentation rib mask is generated by integrating the rib edge map intensity and a prior rib shape model. The prior rib shape model includes a single rib model, and an inter-rib model. The binary segmentation rib mask defines a rib area and a non-rib area in the bone image.

Method 400 also includes, at 440, estimating a first rib signal and a second, different rib signal. The first rib signal is associated with an area in the first energy x-ray image corresponding to the rib area defined by the binary segmentation rib mask. The second, different rib signal is associated with an area in the second energy x-ray image corresponding to the rib area defined by the binary segmentation rib mask. Method 400 may, at 440, estimate the first rib signal and the second rib signal using the binary segmentation rib mask and independent component analysis (ICA). In another embodiment, other, different types of analysis may be employed.

Method 400 also includes, at 450, creating a first energy rib suppressed image by subtracting the first rib signal from the first energy x-ray image. Method 400 may also, at 450, create a second energy rib suppressed image by subtracting the second rib signal from the second energy x-ray image. The first energy rib suppressed image or the second energy rib suppressed image may be registered by example methods and apparatus described herein, or may be used to optimize the registration of the first energy x-ray image with the second energy x-ray image.

Figure 5:
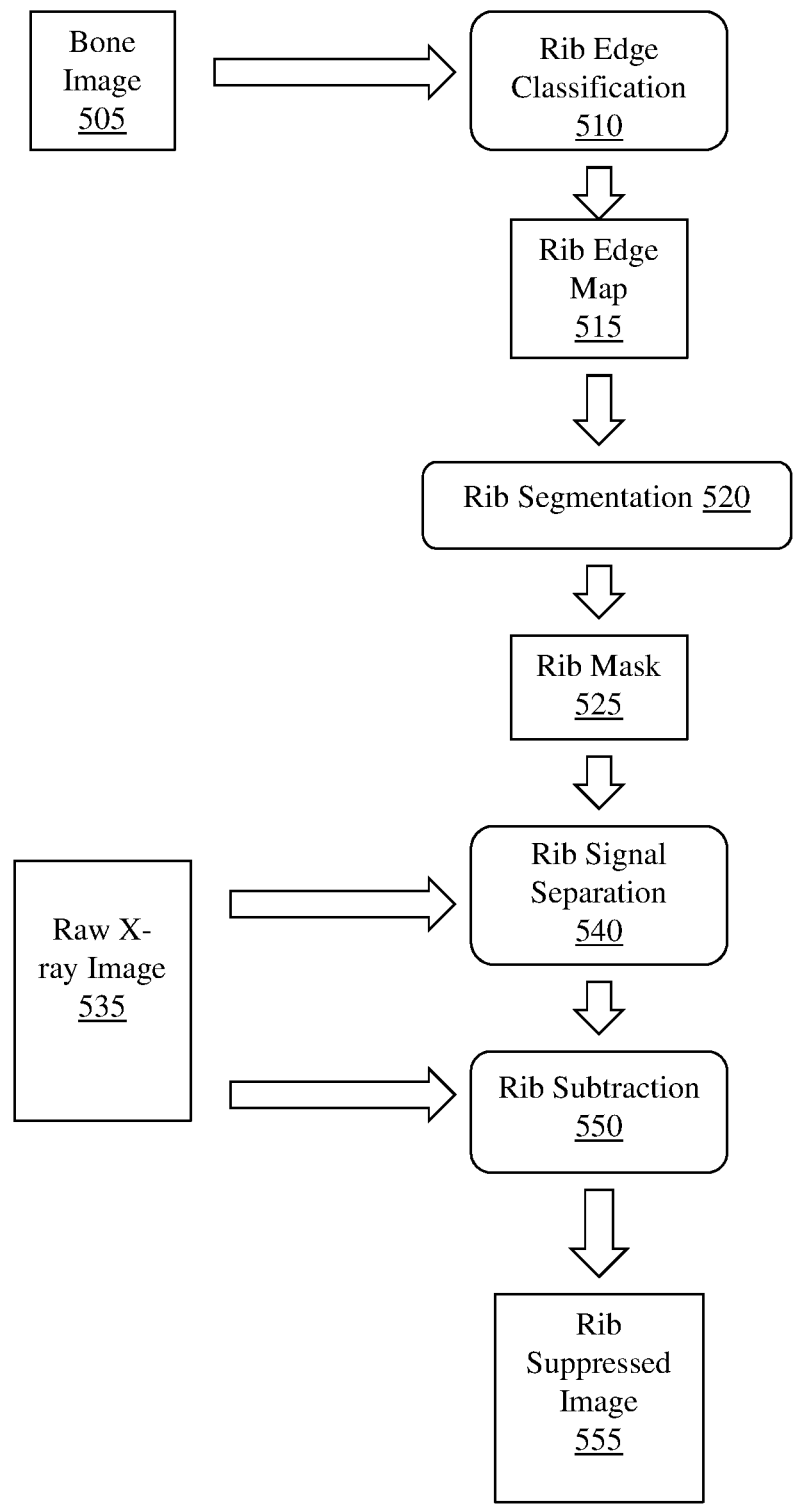
FIG. 5 illustrates an example workflow diagram of an implementation of a method for generating a rib suppressed image.

FIG. 5 illustrates a workflow diagram of an implementation of method 400 suitable for use by example methods and apparatus. FIG. 5 illustrates a bone image 505 being input to rib edge classification process 510. Bone image 505 may be generated based on a set of energy dependent images. Rib edge classification process 510 computes a rib edge map 515 from the bone image 505. Rib edge map 515 is input to rib segmentation process 520. Rib segmentation process 520 generates rib mask 525 from rib edge map 515. Rib mask 525 may be a binary segmentation rib mask. Rib mask 525 is input to rib signal separation process 540. Raw x-ray image 535 is also input to rib signal separation process 540. Raw x-ray image 535 may include a set of energy dependent x-ray images, including a first, low energy x-ray image, and second higher energy x-ray image. Rib signal separation process 540 estimates a signal associated with an area in raw x-ray image 535 that corresponds to a rib area defined by rib mask 525. Rib subtraction process 550, using raw x-ray image 535 and the estimated signal provided by rib signal separation process 540, subtracts the estimated rib signal from raw x-ray image 535 to generate rib suppressed image 555.

Figure 2:
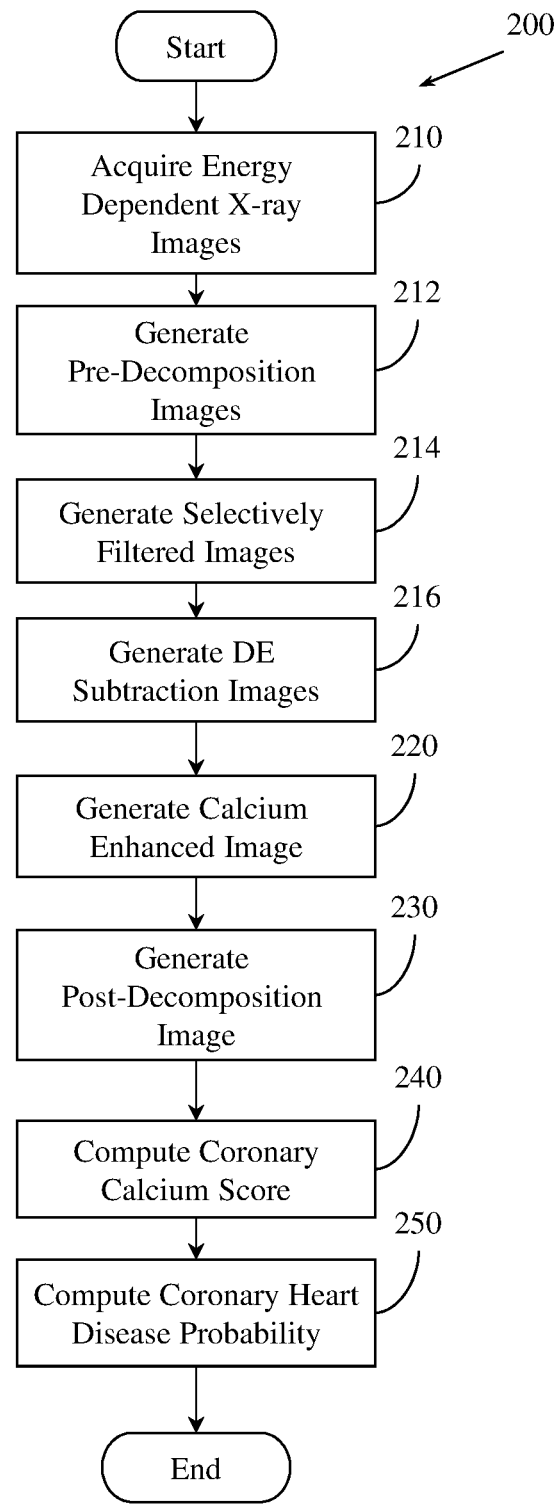
FIG. 2 illustrates an example method of predicting coronary heart disease.

FIG. 2 illustrates an example method 200 of predicting coronary heart disease. Method 200 is similar to method 100, but includes additional details at steps 212, 214, and 216. Method 200 includes, at 210, acquiring a set of energy dependent images of a region of tissue. Step 210 is performed in a manner substantially similar to step 110 of method 100.

Method 200 includes, at 212, generating a set of pre-decomposition images. Method 200 generates the set of pre-decomposition images by pre-decomposition processing the set of energy dependent images. In one embodiment, generating the pre-decomposition image includes normalizing the set of energy dependent images. Normalizing the set of energy dependent images includes normalizing the first energy x-ray image, or correcting the second energy x-ray image.

Generating the set of pre-decomposition images also includes registering the set of energy dependent images or the set of rib suppressed images. Registering the set of energy dependent images or the set of rib suppressed images may include using rigid registration, piece-wise registration, perspective registration, non-rigid registration, anatomy aware registration, or sliding registration. Registration may be based on a parametric motion model or on a deformation field. The deformation field may be computed from the parametric motion model, or from other functions.

Figure 6:
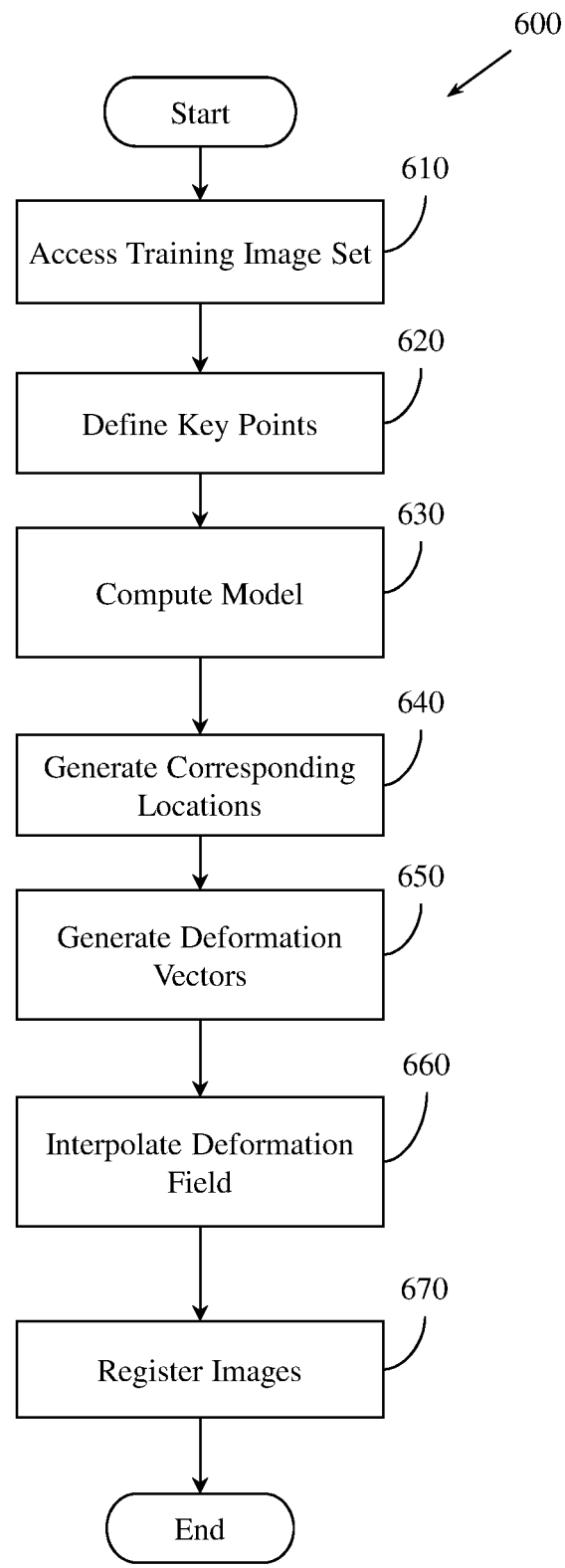
FIG. 6 illustrates an example method for anatomy aware registration.

FIG. 6 illustrates a method 600 for performing anatomy aware registration of a set of energy dependent images or a set of rib suppressed images. Method 600 may be implemented as part of methods and apparatus described herein. Method 600 includes, at 610, accessing a set of training chest x-ray images of a region of tissue. The set of training x-ray images includes a plurality of chest x-ray images.

Method 600 also includes, at 620, defining a set of key points on the set of training chest x-ray images. The set of key points is defined by annotating a set of anatomical landmarks represented in a member of the set of training chest x-ray images. The set of anatomical landmarks may be annotated by an expert pathologist, or may be annotated automatically. The set of key points identifies a set of anatomical landmarks common to at least two members of the plurality of chest x-ray images.

Method 600 also includes, at 630, computing a model based on the set of key points. The model describes a shape of a heart represented in the set of training chest x-ray images.

Method 600 also includes, at 640, generating a set of corresponding locations. Method 600 may generate the set of corresponding locations by detecting, in the first energy x-ray image and the second, different energy x-ray image, a location corresponding to an anatomical landmark represented by a member of the set of key points represented in the model. Method 600 may also generate the set of corresponding locations by detecting in the first energy rib suppressed image and the second energy rib suppressed image, a location corresponding to an anatomical landmark represented by the set of key points.

Method 600 also includes, at 650, generating a set of deformation vectors by computing, for a member of the set of corresponding locations, a deformation vector.

Method 600 also includes, at 660, interpolating a deformation field based, at least in part, on the set of deformation vectors. In one embodiment, the deformation field is defined using a B-spline interpolation. In another embodiment, the deformation field is defined using other, different interpolation approaches.

Method 600 also includes, at 670, registering the first energy x-ray image and the second, different energy x-ray image, using the deformation field. Method 600, at 670, may also register the first energy rib suppressed image and the second energy rib suppressed image, using the deformation field.

Figure 7:
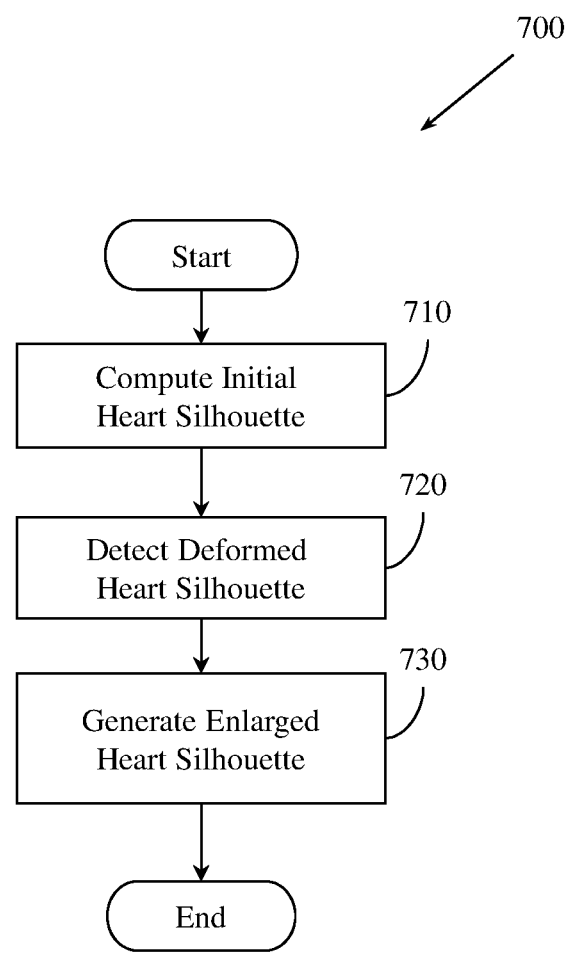
FIG. 7 illustrates an example method of generating a heart silhouette.

In one embodiment, method 100 may generate a binary mask. The binary mask defines an area inside a heart silhouette and an area outside the heart silhouette. FIG. 7 illustrates a method 700 for generating a binary mask. Method 700 may be implemented as part of methods and apparatus described herein. Method 700 includes, at 710 computing an initial heart silhouette based on the first energy x-ray image or the first energy rib suppressed image. In one embodiment, the initial heart silhouette is computed using dynamic programming. In another embodiment, the initial heart silhouette may be computed using other techniques.

Method 700 also includes, at 720, detecting a deformed heart silhouette in the second energy x-ray image or the second energy rib suppressed image.

Method 700 also includes, at 730, generating an enlarged heart silhouette by dilating the initial heart silhouette. The initial heart silhouette may be dilated using a margin. The enlarged heart silhouette covers the deformed heart silhouette. The binary mask generated from the heart silhouette may be used as an input for the registration methods or techniques described herein.

Figure 8:
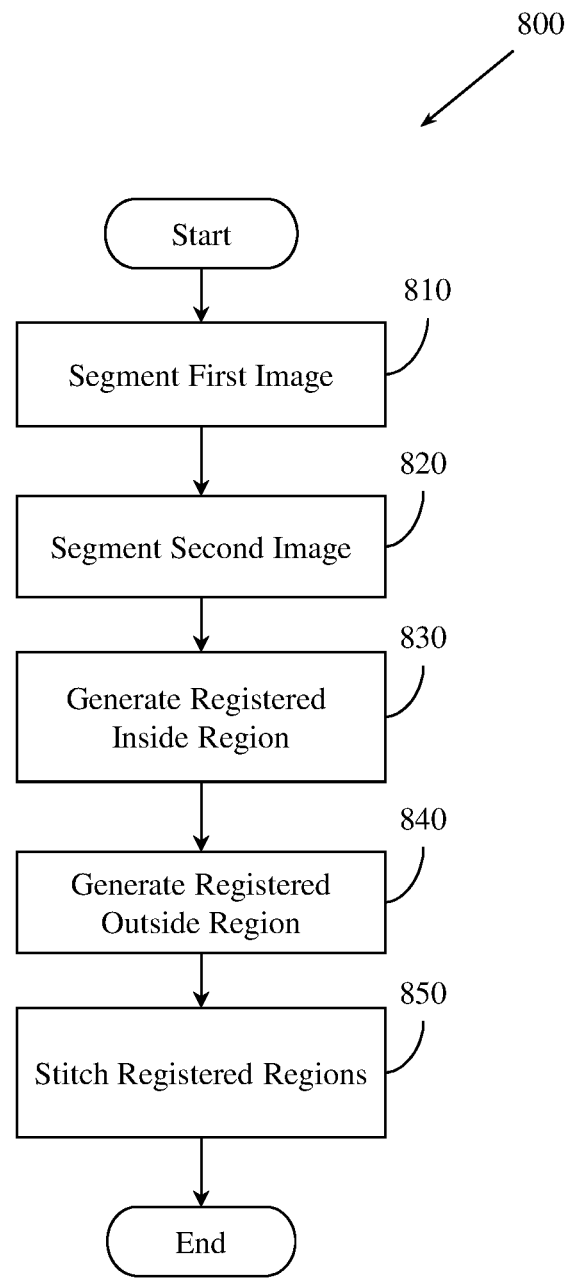
FIG. 8 illustrates an example method of sliding registration.

FIG. 8 illustrates an example method 800 of sliding registration. Method 800 may be employed with method 100, method 200, or other methods and apparatus described herein. Method 800 may be employed to register the set of energy dependent images, or the set of rib suppressed images. In one embodiment, the binary mask generated by method 700 may be used as an input to method 800. Method 800 includes, at 810 segmenting the first energy x-ray image or the first energy rib suppressed image into a first inside region and a first outside region using the binary mask. The first inside region defines an area of the first energy x-ray image or the first energy rib suppressed image inside the heart silhouette defined by the binary mask. The first outside region defines an area of the first energy x-ray image or the first energy rib suppressed image outside the heart silhouette defined by the binary mask.

Method 800 also includes, at 820, segmenting the second energy x-ray image or the second energy rib suppressed image into a second inside region and a second outside region using the binary mask. The second inside region defines an area of the second energy x-ray image or the second energy rib suppressed image inside the heart silhouette defined by the binary mask. The second outside region defines an area of the second energy x-ray image or the second energy rib suppressed image outside the heart silhouette defined by the binary mask.

Method 800 also includes, at 830, generating a registered inside region by registering the first inside region with the second inside region using free form deformation (FFD) registration. In one embodiment, FFD registration of the first inside region with the second inside region includes parameterizing a motion field between the first energy x-ray image and the second energy x-ray image. FFD registration may also include parameterizing a motion field between the first energy rib suppressed image and the second energy rib suppressed image. Method 800 parameterizes the motion field by interpolating a series of B-spline basis functions with a mesh of uniform spacing control points, and by minimizing a masked FFD registration cost function. The masked FFD registration cost function is masked using the binary mask.

Method 800 also includes, at 840, generating a registered outside region by registering the first outside region with the second outside region using rigid deformation registration. In another embodiment, other registration approaches may be used to register the first outside region with the second outside region.

Method 800 also includes, at 850, stitching the registered inside region with the registered outside region. The registered inside region and the registered outside region may be stitched using soft weighting. In another embodiment, other techniques may be used to stitch the registered inside region with the registered outside region.

Method 200 also includes, at 214, generating a set of selectively filtered images. Method 200 generates the set of selectively filtered images by selectively filtering the set of pre-decomposition images. In one embodiment, generating the set of selectively filtered images includes filtering the first energy x-ray image or the first energy rib suppressed image using a Gaussian filter. Generating the set of selectively filtered images also includes filtering the second energy x-ray image or the second energy rib suppressed image. The second energy x-ray image or the second energy rib suppressed image may be filtered using a vesselness operator using morphological suppression. The second energy x-ray image or the second energy rib suppressed image may also be filtered using a directional low pass filter.

In one embodiment, filtering the second energy x-ray image or the second energy rib suppressed image using a directional low pass filter includes generating a set of directional band-pass filters. Filtering the second energy x-ray image or the second energy rib suppressed image using a directional low pass filter also includes producing a vector of filter responses by convolving the second energy x-ray image or the second energy rib suppressed image with the set of directional band-pass filters, where a filter response is associated with a channel. Filtering the second energy x-ray image or the second energy rib suppressed image using a directional low pass filter also includes producing a transformed vector of filter responses by multiplying a filter response in the vector of filter responses by a weighting coefficient. The weighting coefficient amplifies a selective width associated with the filter response or a selective direction associated with the filter response. The weighting coefficient may also suppress the selective width or the selective direction associated with the filter response. Filtering the second energy x-ray image or the second energy rib suppressed image using a directional low pass filter also includes filtering the second energy x-ray image or the second energy rib suppressed image based, at least in part, on the transformed filter response vector.

Method 200 also includes, at 216, generating a set of DE subtraction images. Method 200 generates the set of DE subtraction images by dual energy decomposing the set of selectively filtered images. In one embodiment, generating the set of dual energy subtraction images includes correcting the set of selectively filtered images by removing scatter from a member of the set of selectively filtered images.

Example methods and apparatus may perform scatter estimation and removal. In one embodiment, an estimate of scatter at a location in a member of the set of selectively filtered images is obtained. A scatter estimation model with the member of the set of selectively filtered images is trained by fitting scatter measurements to a mathematical function. The mathematical function may be the convolution result of the original image by a low pass filter, or the morphing of a best-fitting scatter surface from a dictionary of scatter surfaces. Scatter measurements may be obtained from radiation measurements under small lead beam blocks placed near the output port of an x-ray tube used to acquire the set of energy dependent images. Under the beam block, there is no primary radiation, only scattered radiation. At an edge of a member of the set of energy dependent images, for example, under the lead collimation, example methods and apparatus may also measure scatter in the same manner as with the beam blocks. The dictionary of scatter surfaces may be created using Monte Carlo simulations from computed tomography 3D volumes. The dictionary of scatter surfaces may be generated by example methods and apparatus, and may be stored in a computer memory, acquired across a network, from the cloud, or by other techniques. In one embodiment, the dictionary of scatter surfaces is predefined. Example methods and apparatus subtract the result from the original member of the set of selectively filtered images to get a new, scatter free image.

Example methods and apparatus obtain templates for scatter by imaging a number of patients of varying body size with a high density of beam blocks. Functions are then fit to the beam blocks. Matching to templates is then performed by body size and by values under the same beam blocks. Example methods and apparatus may scale or morph the beam templates to estimate scatter throughout the member of the set of selectively filtered images.

One embodiment of methods and apparatus described herein may include a small step wedge having different calcium concentrations placed in the heart field to obtain a calibration curve of intensity versus calcium concentration.

Method 200 also includes at 220, generating a calcium enhanced image. Method 200 generates the calcium enhanced image based, at least in part, on the set of DE subtraction images. Step 220 may be performed substantially similarly to step 120 of method 100.

Method 200 also includes, at 230, generating a post-decomposition image. Method 200 generates the post-decomposition based, at least in part, on the calcium enhanced image. In one embodiment, generating the post-decomposition image includes applying un-sharp masking to the set of dual energy subtraction images. The un-sharp masking is based, at least in part, on the set of dual energy subtraction images, an un-sharp coefficient, and a low-pass filtering operation. In one embodiment, the value of the un-sharp coefficient is within [0, 1). In another embodiment, the un-sharp coefficient may have other values. Step 230 may be performed substantially similarly to step 130 of method 100.

In one embodiment, generating the post-decomposition image includes selectively adjusting the dynamic range of the set of dual energy subtraction images. Method 200 may adjust the dynamic range of the set of dual energy subtraction images to match, within a threshold amount, the dynamic range of a display device format or a storage device format. The threshold amount may be adjustable by a user. For example, method 200 may adjust the dynamic range of the set of dual energy subtraction images by a first amount to match the dynamic range of a first display device, and may adjust the dynamic range of the set of dual energy subtraction images by a second, different amount to match the dynamic range of a second, different display device.

Method 200 also includes, at 240, computing a coronary calcium score. The coronary calcium score is based, at least in part, on the post-decomposition image. In one embodiment, computing the coronary calcium score includes extracting a set of features from the post-decomposition image, relating the set of features to a set of vessel-territory specific CT calcium scores, and computing the coronary calcium score. The coronary calcium score is based, at least in part, on the relation of the set of features to the set of vessel-territory specific CT calcium scores. Step 240 may be performed in a manner substantially similar to step 140 of method 100.

In one embodiment, method 200 may compute the calcium score based on coronary calcium represented in DE x-ray images. Example methods and apparatus extract features from DE x-ray images and relate results to corresponding vessel-territory-specific CT calcium scores using support vector machine (SVM) regression. In one embodiment, a physician may draw a free-hand loop encircling a region of interest in an image, including the RCA, LAD, LCX, or LM. Example methods and apparatus may then extract features from the region of interest and apply SVM regression to determine a calcium score. In another embodiment, the region of interest is identified automatically, and the features may be extracted automatically.

SVM regression may include analyzing a number of features. The number of features may include an exposure time feature. Thicker subjects will have a longer exposure time. Thus, the exposure time feature facilitates accounting for scatter and beam hardening effects.

The number of features may also include an exposure time/log(intensity) feature in the second energy x-ray image, where intensity is an estimate of intensity in the heart region. The exposure time/log(intensity) feature provides a more accurate measure of subject thickness than conventional approaches. The number of features may also include a vesselness filtering feature. Vesselness filtering enhances features in calcified arteries compared to conventional approaches. The number of features may also include a multi-scale filtering feature, a segmented calcium deposits feature based upon vessel like negative excursions, or an average intensity of the segmented calcification in the coronary calcium image feature.

The number of features may also include features derived from a bone image, or from other images, where the other images are processed with a variety of settings for scatter removal, creating a range of images. In one embodiment, the range of images may include five to ten images. From the range of images, example methods and apparatus extract contrast values for calcium and other properties of the range of images. In another embodiment, the range of images may include a different number of images, or other features may be extracted from the range of images.

The number of features may also include a texture feature, a shape feature, a curvedness feature, or a computed feature, where the computed feature is based on images including a bone image, a soft tissue image, a high kV image, a low kV image, or a calcification deposits image. The computed feature may include a maximum in the calcification feature, a minimum in the calcification feature, a background subtracted maximum feature, a background subtracted minimum feature, or a vesselness feature.

Method 200 also includes, at 250, computing a coronary heart disease probability. The coronary heart disease probability is based, at least in part, on the coronary calcium score. Method 200 may perform step 250 in a manner substantially similar to step 150 of method 100.

Figure 3:
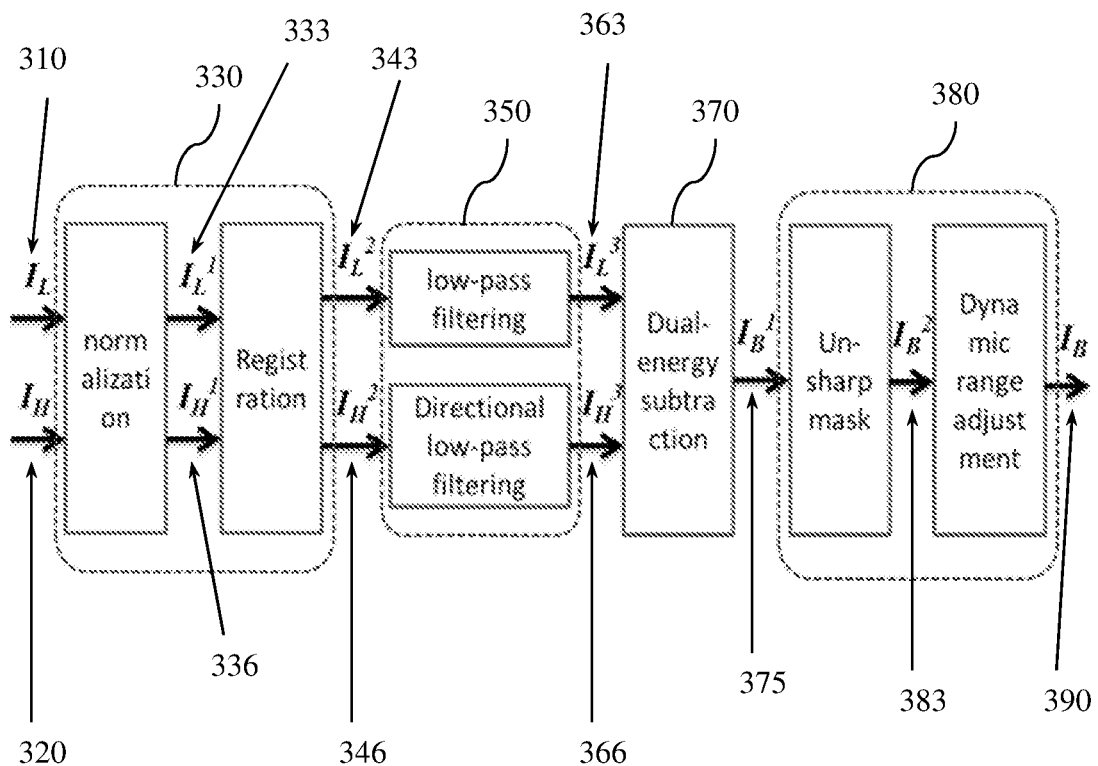
FIG. 3 illustrates an example workflow diagram of predicting coronary heart disease.

FIG. 3 illustrates a workflow diagram of an implementation of methods and apparatus described herein. FIG. 3 illustrates a low energy x-ray image $I_L$ 310 and a high energy x-ray image $I_H$ 320 being input to a pre-decomposition process 330. Pre-decomposition process 330 normalizes low energy x-ray image $I_L$ 310 and high energy x-ray image $I_H$ 320 to produce normalized low energy x-ray image $I_L^1$ 333 and normalized high energy x-ray image $I_H^1$ 336. Pre-decomposition process 330 registers normalized low energy x-ray image $I_L^1$ 333 and normalized high energy x-ray image $I_H^1$ 336 to produce registered low energy x-ray image $I_L^2$ 343 and registered high energy x-ray image $I_H^2$ 346. Registered low energy x-ray image $I_L^2$ 343 and registered high energy x-ray image $I_H^2$ 346 are input to selective filtering process 350. Selective filtering process 350 applies low-pass filtering to registered low energy x-ray image $I_L^2$ 343 to produce filtered low energy x-ray image $I_L^3$ 363. Selective filtering process 350 applies directional low-pass filtering to registered high energy x-ray image $I_H^2$ 346 to produce filtered high energy x-ray image $I_H^3$ 366. Filtered low energy x-ray image $I_L^3$ 363 and filtered high energy x-ray image $I_H^3$ 366 are input to dual energy subtraction process 370. Dual energy subtraction process 370 eliminates soft-tissue anatomic structures from filtered low energy x-ray image $I_L^3$ 363 and filtered high energy x-ray image $I_H^3$ 366 to produce first bone image $I_B^1$ 375. First bone image $I_B^1$ 375 is provided as an input to post-decomposition process 380. Post decomposition process 380 applies un-sharp masking to first bone image $I_B^1$ 375 to produce second bone image $I_B^2$ 383. Post decomposition process 380 applies dynamic range adjustment to second bone image $I_B^2$ 383 to produce final bone image image $I_B$ 390.

Figure 9:
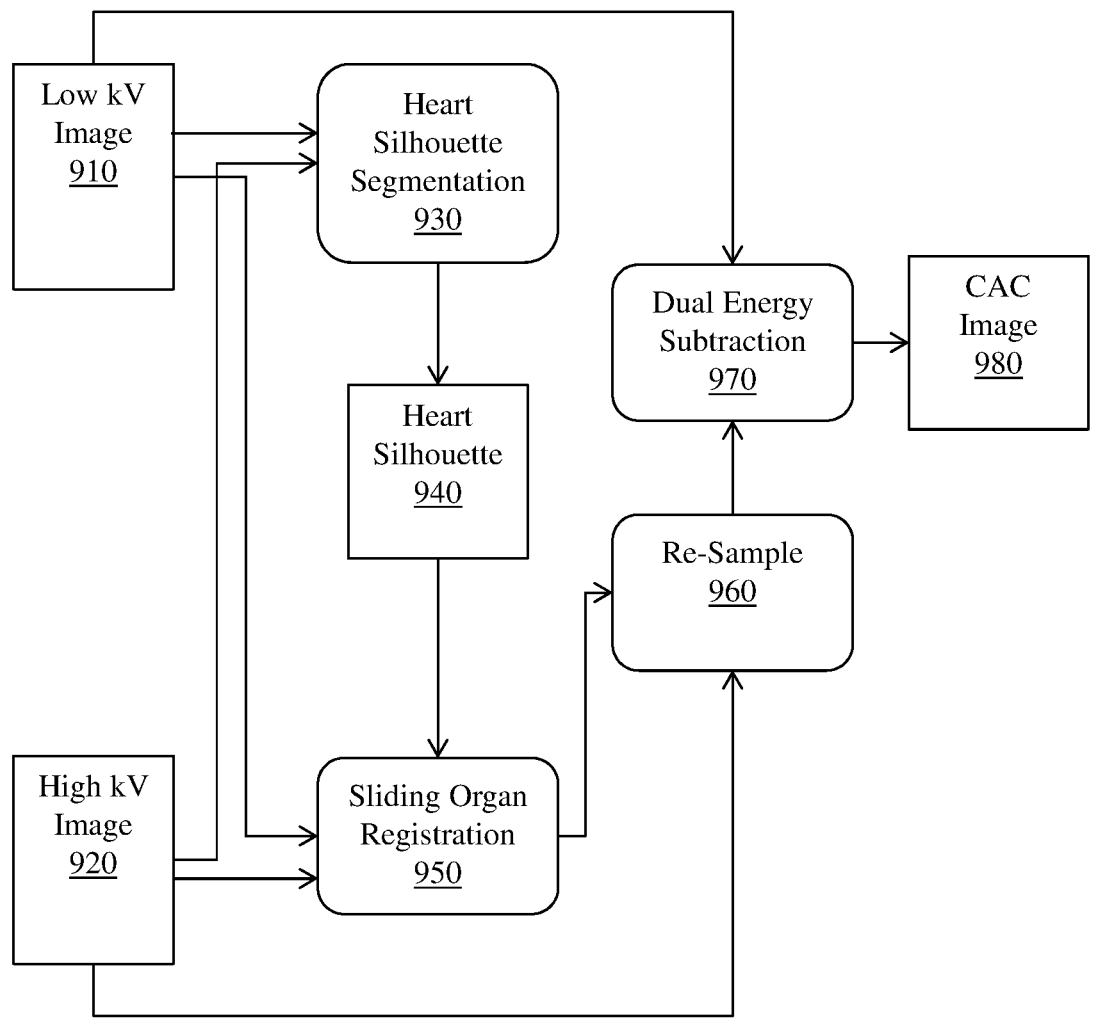
FIG. 9 illustrates an example workflow diagram of an implementation of a method for predicting coronary heart disease using a heart silhouette and sliding registration.

FIG. 9 illustrates a workflow diagram of an implementation of methods and apparatus described herein using heart silhouette segmentation and sliding registration to generate a CAC image. A low kV image 910 and a high kV image 920 are input to heart silhouette segmentation process 930. Heart silhouette segmentation process 930 generates heart silhouette 940 from low kV image 910 and high kV image 920 using dynamic programming. Heart silhouette 940 may be generated using, for example, method 700. FIG. 9 also illustrates low kV image 910 and high kV image 920 being input to sliding organ registration process 950. Heart silhouette 940 is also input to sliding organ registration process 950. Sliding organ registration process 950 computes a motion field or a deformation field and registers high kV image 920 with kV image 910 using sliding registration. Sliding organ registration process 950 may register high kV image 920 with kV image 910 using, for example, sliding registration method 800. Sliding organ registration process 950 improves on conventional approaches to registering a high kV image with a low kV image by using heart silhouette 940 to constrain optimization such that non-rigid deformation is only performed inside the areas of low kV image 910 and high kV image 920 corresponding to the heart silhouette defined by heart silhouette 940. Sliding organ registration process 950 registers the areas of low kV image 910 and high kV image 920 corresponding to the heart silhouette defined by heart silhouette 940 using a different deformation than that used to register the areas of low kV image 910 and high kV image 920 corresponding to the region outside the heart silhouette defined by heart silhouette 940. Sliding organ registration process 950 provides the registered image to re-sample process 960. Re-sample process 960 re-samples the registered image. The re-sampled registered image is provided to dual energy subtraction process 970. Low kV image 910 is also provided to dual energy subtraction process 970. Dual energy subtraction process 970 performs material decomposition on the re-sampled registered image and low kV image 910 to eliminate soft tissue anatomic structures that distract from the diagnosis of coronary artery calcification. Dual energy subtraction process 970 outputs CAC image 980.

Figure 10:
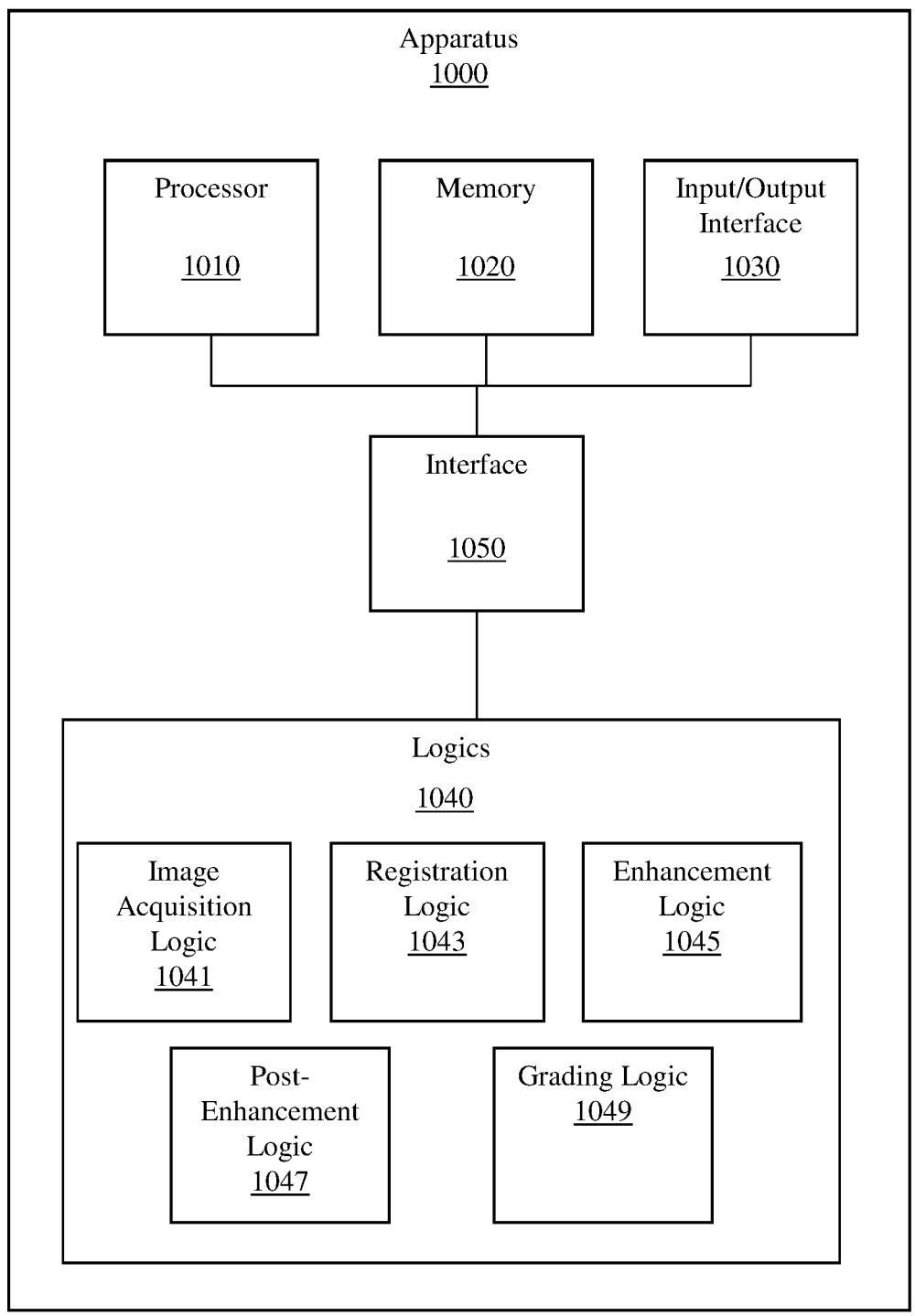
FIG. 10 illustrates an example apparatus that grades coronary calcium.

FIG. 10 illustrates an apparatus 1000 for grading coronary calcium. Apparatus 1000 includes a processor 1010, a memory 1020, an input/output (IO) interface 1030, a set of logics 1040, and an interface 1050 that connects the processor 1010, the memory 1020, the IO interface 1030, and the set of logics 1040. Memory 1020 may store a set of radiographic images or set of vessel-territory-specific CT coronary calcium images.

The set of logics 1040 comprises an image acquisition logic 1041, a registration logic 1043, an enhancement logic 1045, a post-enhancement logic 1047, and a grading logic 1049. The image acquisition logic 1041 acquires a set of radiographic images of a region of tissue. The set of radiographic images may be provided by a dual energy x-ray image system, or by another imaging system. The set of radiographic images includes a low-energy reference x-ray image and a higher-energy floating x-ray image. The region of tissue includes a heart, a coronary artery, a pulmonary artery, an aorta, or an aortic valve. At least two members of the set of radiographic images are oblique views. In one embodiment, image acquisition logic 1041 acquires the set of radiographic images using a flat panel x-ray detector employing rapid kV switching, rapid kV and mA switching, rapid kV switching with EKG triggering, or rapid kV and mA switching with EKG triggering.

The registration logic 1043 produces a set of registered images from a plurality of members of the set of radiographic images. Registration logic 1043 produces the set of registered images by defining a parametric motion model or a deformation field on the higher-energy floating x-ray image, and by deforming the higher-energy floating x-ray image to the low energy reference x-ray image using sliding organ registration, anatomy aware registration, rigid registration, piece-wise registration, perspective registration, or non-rigid registration, based on the parametric motion model or the deformation field. In one embodiment, registration logic 1043 produces a set of rib suppressed images from a member of the set of radiographic images.

The enhancement logic 1045 produces a set of calcium-enhanced images from the set of registered images. Enhancement logic 1047 produces the set of calcium-enhanced images from the set of registered images by producing a set of filtered images by selectively low-pass filtering or selectively directionally low-pass filtering the set of registered images. Enhancement logic 1047 also materially decomposes the set of filtered images.

The post-enhancement logic 1047 produces a bone image based, at least in part, on the set of calcium-enhanced images. Post-enhancement logic 1047 produces the bone image by unsharp-masking the set of calcium-enhanced images or by adjusting the dynamic range of the set of calcium-enhanced images.

The grading logic 1049 computes a coronary heart disease prediction score based, at least in part, on the bone image. Grading logic 1049 trains a support vector machine (SVM) on a set of vessel-territory-specific CT coronary calcium images. Grading logic 1049 automatically computes the coronary heart disease prediction score by extracting a set of features from the bone image or the set of radiographic images, and by applying SVM regression to the set of features using the SVM. The set of features may include a shape feature, a texture feature, a curvedness feature, a contrast feature, an exposure time feature, and exposure time/log(intensity) feature, or a vesselness feature.

In one embodiment, the set of logics 1040 may include an optimization logic. The optimization logic optimizes the registration logic 1043 by computing a value for an objective function. The value for the objective functions is computed as a function of a similarity measurement of the low-energy reference x-ray image and the higher-energy floating x-ray image, and a regularization term that penalizes motion model parameters that are outside a threshold range. The threshold range may be user adjustable.

In one embodiment, the set of logics 1040 may include a display logic. The display logic displays the bone image, the set of calcium enhanced images, the set of registered images, the set of radiological images, or the coronary heart disease prediction score. Displaying the bone image, the set of calcium enhanced images, the set of registered images, the set of radiological images, or the coronary heart disease prediction score may also include printing or storing in a non-transitory computer storage device or computer memory the bone image, the set of calcium enhanced images, the set of registered images, the set of radiological images, or the coronary heart disease prediction score. The display logic may control a computer assisted diagnostic (CADx) system to display the bone image, the set of calcium enhanced images, the set of registered images, the set of radiological images, or the coronary heart disease prediction score. By displaying the bone image, the set of calcium enhanced images, the set of registered images, the set of radiological images, or the coronary heart disease prediction score, example apparatus provide a timely and intuitive way for a human pathologist to more accurately classify pathologies demonstrated by a patient, thus improving on conventional approaches to characterizing coronary artery calcium, or predicting coronary artery disease.

Figure 11:
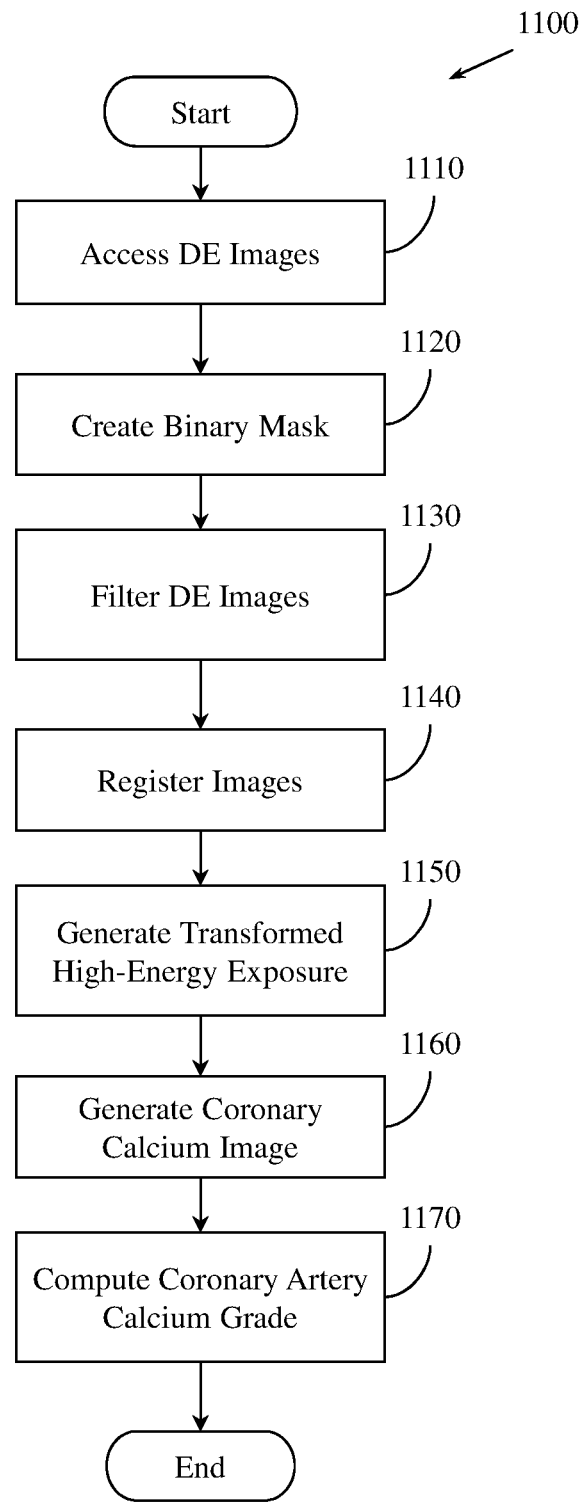
FIG. 11 illustrates an example method for grading CAC.

FIG. 11 illustrates a method 1100 for grading CAC. Method 1100 includes, at 1110, accessing a set of dual-energy (DE) chest radiography images of a region of tissue. The set of DE chest radiography images includes a first, low-energy exposure and a second, high-energy exposure. The first, low energy exposure may be a reference image. The second, high-energy exposure may be a floating image.

Method 1100 also includes, at 1120, creating a binary mask by segmenting a heart silhouette represented in the region of tissue. The binary mask may define a region inside the heart silhouette, and a region outside the heart silhouette.

Method 1100 also includes, at 1130, filtering noise from the set of DE chest radiography images. Filtering noise from the set of DE chest radiography images may include selectively applying low-pass filtering or directional low-pass filtering to the set of DE chest radiography images.

Method 1100 also includes, at 1140, registering the first, low-energy exposure with the second, high-energy exposure. Method 1100 may, at 1140, register the first, low-energy exposure with the second, high-energy exposure using sliding organ registration or anatomy aware registration. In one embodiment, registration is based, at least in part, on the binary mask.

Method 1100 also includes, at 1150, generating a transformed high-energy exposure by re-sampling the second, high-energy exposure.

Method 1110 also includes, at 1160, generating a coronary calcium image (CCI) by performing dual-energy subtraction on the first, low-energy exposure and the transformed high-energy exposure.

Method 1110 also includes, at 1170, computing a CAC grade based, at least in part, on the CCI. The CAC grade may be computed using SVM regression based on a set of features extracted from the CCI, and a set of training CT coronary calcium images.

Figure 12:
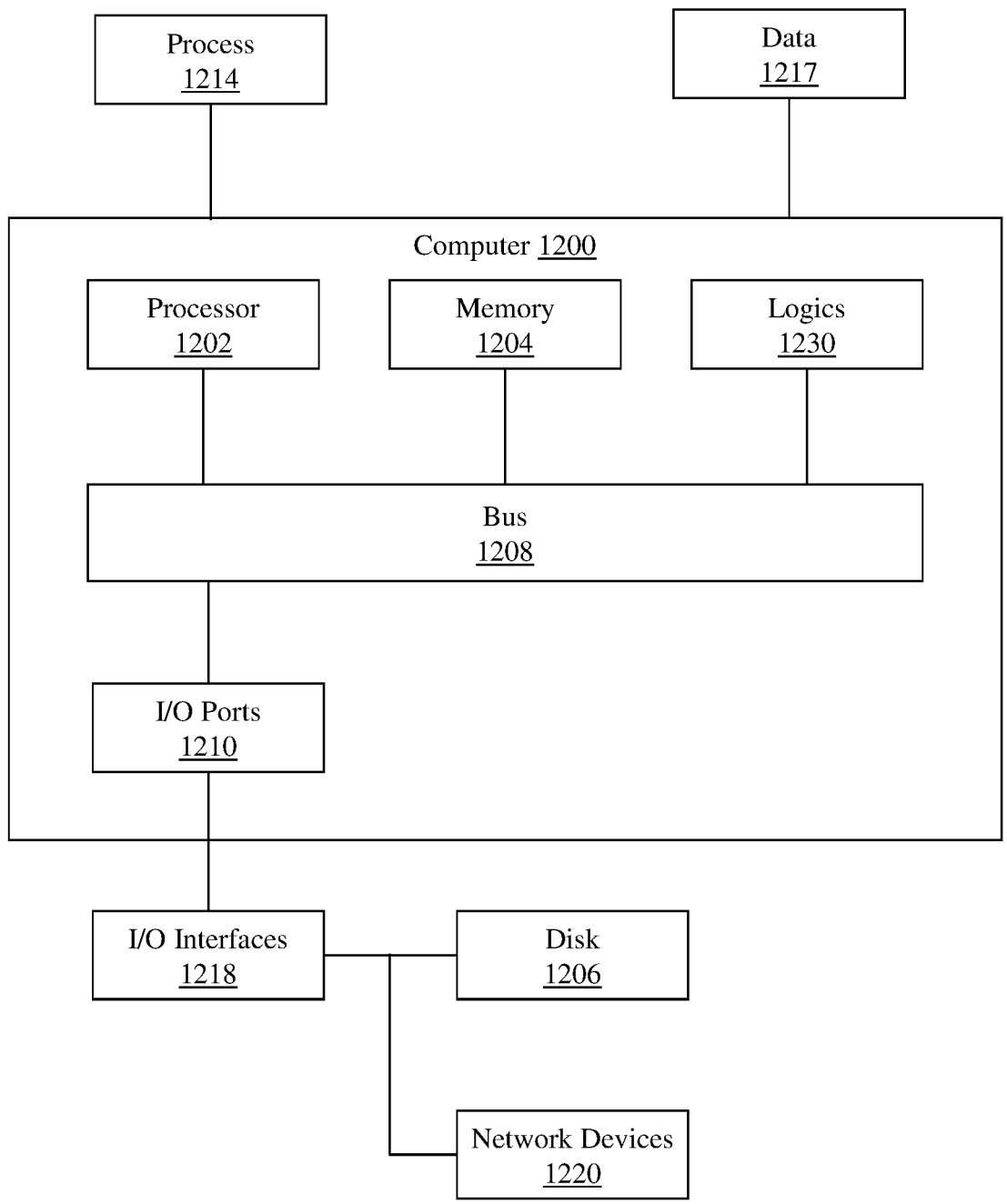
FIG. 12 illustrates an example computer in which example methods and apparatus described herein operate.

FIG. 12 illustrates an example computer 1200 in which example methods illustrated herein can operate and in which example logics may be implemented. In different examples, computer 1200 may be part of an x-ray or radiographic system, may be operably connectable to an x-ray or radiographic system, or may be part of a CADx system.

Computer 1200 includes a processor 1202, a memory 1204, and input/output ports 1210 operably connected by a bus 1208. In one example, computer 1200 may include a set of logics 1230 that perform a method of predicting coronary heart disease. Thus, the set of logics 1230, whether implemented in computer 1200 as hardware, firmware, and/or a combination thereof may provide means (e.g., hardware, circuits) for predicting coronary heart disease. In different examples, the set of logics 1230 may be permanently and/or removably attached to computer 1200. In one embodiment, the functionality associated with the set of logics 1230 may be performed, at least in part, by hardware logic components including, but not limited to, field-programmable gate arrays (FPGAs), application specific integrated circuits (ASICs), application specific standard products (ASSPs), system on a chip systems (SOCs), or complex programmable logic devices (CPLDs). In one embodiment, individual members of the set of logics 1230 are implemented as ASICs or SOCs.

Processor 1202 can be a variety of various processors including dual microprocessor and other multi-processor architectures. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, a solid state device (SSD), or a memory stick. Furthermore, disk 1206 may include optical drives like a CD-ROM or a digital video ROM drive (DVD ROM). Memory 1204 can store processes 1214 or data 1217, for example. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, logics, and peripherals using other busses that are not illustrated (e.g., PCIE, SATA, Infiniband, 1394, USB, Ethernet).

Computer 1200 may interact with input/output devices via I/O interfaces 1218 and input/output ports 1210. Input/output devices can include, but are not limited to, DE digital radiography x-ray systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network.

Through the network, computer 1200 may be logically connected to remote computers. The networks with which computer 1200 may interact include, but are not limited to, a local area network (LAN), a wide area network (WAN), or other networks.

The following includes definitions of selected terms employed herein. The definitions include various examples and/or forms of components that fall within the scope of a term and that may be used for implementation. The examples are not intended to be limiting. Both singular and plural forms of terms may be within the definitions.

References to "one embodiment", "an embodiment", "one example", "an example", and other similar exemplary language indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic device, an application specific integrated circuit (ASIC), a compact disk (CD), other optical device, a random access memory (RAM), a read only memory (ROM), a memory chip or card, a memory stick, and other media or device from which a computer, a processor or other electronic device can read.

"Logic", as used herein, includes but is not limited to hardware, or firmware, or combinations of each to perform a function(s) or an action(s), or to cause a function or action from another logic, method, or system. Logic may include a software controlled microprocessor, a discrete logic (e.g., ASIC), an analog circuit, a digital circuit, a programmed logic device, a memory device containing instructions, and other physical devices. Logic may include one or more gates, combinations of gates, or other circuit components. Where multiple logical logics are described, it may be possible to incorporate the multiple logical logics into one physical logic. Similarly, where a single logical logic is described, it may be possible to distribute that single logical logic between multiple physical logics.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer executable instructions that when executed by a computer control the computer to perform a method for predicting coronary heart disease, the method comprising:
   acquiring a set of energy dependent images of a region of tissue, where the set of images includes a first energy x-ray image and a second, different energy x-ray image;
   generating a set of rib suppressed images based on the set of energy dependent images, where the set of rib suppressed images includes a first energy rib suppressed image and a second energy rib suppressed image;
   generating a calcium-enhanced image of the region of tissue, where generating the calcium-enhanced image includes:
      generating a set of pre-decomposition images by pre-decomposition processing the set of energy dependent images, where generating the set of pre-decomposition images includes registering the set of energy dependent images or the set of rib suppressed images using anatomy aware registration;
      generating a set of selectively filtered images by selectively filtering the set of pre-decomposition images; and
      generating a set of dual energy subtraction images by dual energy decomposing the set of selectively filtered images;
   generating a post-decomposition image based, at least in part, on the calcium-enhanced image;
   computing a coronary calcium score based, at least in part, on the post-decomposition image; and
   computing a coronary heart disease probability based, at least in part, on the coronary calcium score;
   where registering the set of energy dependent images or rib suppressed images using anatomy aware registration includes:
      accessing a set of training chest x-ray images of a region of tissue, where the set of training chest x-ray images includes a plurality of chest x-ray images;
      defining a set of key points based on the set of training chest x-ray images, where the set of key points is defined by annotating a set of anatomical landmarks represented in a member of the set of training chest x-ray images, where the set of key points identifies a set of anatomical landmarks common to at least two members of the plurality of chest x-ray images;

computing a model based on the set of key points, where the model describes a shape of a heart represented in the set of training chest x-ray images;

generating a set of corresponding locations by detecting, in the first energy x-ray image and the second, different energy x-ray image, or in the first energy rib suppressed image and the second energy rib suppressed image, a location corresponding to an anatomical landmark represented by the set of key points;

generating a set of deformation vectors by computing, for a member of the set of corresponding locations, a deformation vector;

interpolating a deformation field based, at least in part, on the set of deformation vectors, where the deformation field is defined using a B-spline interpolation; and registering the first energy x-ray image and the second, different energy x-ray image, or the first energy rib suppressed image and the second energy rib suppressed image, using the deformation field.

2. The non-transitory computer-readable storage device of claim 1, where the first energy x-ray image is a 60 kV exposure and the second, different energy x-ray image is a 120 kV exposure, where the first energy x-ray image and the second, different energy x-ray image are acquired within a 150 ms interval.

3. The non-transitory computer-readable storage device of claim 1, where acquiring the set of energy dependent images includes creating a high x-ray spectrum and a low x-ray spectrum by switching kV between a first, high kV value, and a second, lower kV value, where the first, high kV value is 120 kV, and the second, lower kV value is 60 kV.

4. The non-transitory computer-readable storage device of claim 1, where acquiring the set of energy dependent images includes creating a high x-ray spectrum and a low x-ray spectrum by switching kV and mA, by switching pre-filtration x-ray filters, or by switching pre-filtration x-ray filters and kV.

5. The non-transitory computer-readable storage device of claim 1, where the set of energy dependent images is acquired using a photon counting, energy sensitive detector, or by using a sandwich detector comprising a first detector and a second different detector, where the first energy x-ray image is acquired using the first detector, and the second energy x-ray image is acquired using the second detector.

6. The non-transitory computer-readable storage device of claim 1, where generating the set of pre-decomposition images includes normalizing the set of energy dependent images, where normalizing the set of energy dependent images includes normalizing the first energy x-ray image, or correcting the second energy x-ray image.

7. The non-transitory computer-readable storage device of claim 1, where generating the set of rib suppressed images includes:

generating a bone image of the region of tissue based on the set of energy dependent images, where the bone image includes a plurality of pixels;

computing a rib edge map based on the bone image, where the rib edge map is computed using an edge filter, or where the rib edge map is computed using a convolutional neural network trained on a set of rib-annotated images using a supervised machine learning process, where the rib edge map displays a probability of rib edge occurrence at a pixel within the bone image, and where the rib edge map has an intensity;

generating a binary segmentation rib mask based on the rib edge map by integrating the rib edge map intensity and a prior rib shape model, where the prior rib shape model includes a single rib model and an inter-rib model, and where the binary segmentation rib mask defines a rib area and a non-rib area in the bone image;

estimating, using the binary segmentation rib mask and independent component analysis (ICA), a first rib signal associated with an area in the first energy x-ray image corresponding to the rib area, and a second, different rib signal associated with an area in the second energy x-ray image corresponding to the rib area; and creating the first energy rib suppressed image by subtracting the first rib signal from the first energy x-ray image, or creating the second energy rib suppressed image by subtracting the second rib signal from the second energy x-ray image.

8. The non-transitory computer-readable storage device of claim 7, where generating the set of pre-decomposition images includes registering the set of energy dependent images or the set of rib suppressed images using rigid registration, piece-wise registration, perspective registration, non-rigid registration, or sliding registration.

9. The non-transitory computer-readable storage device of claim 8, the method further comprising generating a binary mask that defines an area inside a heart silhouette and an area outside the heart silhouette, where generating the binary mask includes:

computing an initial heart silhouette based on the first energy x-ray image or the first energy rib suppressed image, where the initial heart silhouette is computed using dynamic programming;

detecting a deformed heart silhouette in the second energy x-ray image or the second energy rib suppressed image; and generating an enlarged heart silhouette by dilating the initial heart silhouette using a margin, where the enlarged heart silhouette covers the deformed heart silhouette.

10. The non-transitory computer-readable storage device of claim 9, where registering the set of energy dependent images or the set of rib suppressed images using sliding registration includes:

segmenting the first energy x-ray image or the first energy rib suppressed image into a first inside region and a first outside region using the binary mask, where the first inside region defines an area of the first energy x-ray image or the first energy rib suppressed image inside the heart silhouette defined by the binary mask, and the first outside region defines an area of the first energy x-ray image or the first energy rib suppressed image outside the heart silhouette defined by the binary mask;

segmenting the second energy x-ray image or the second energy rib suppressed image into a second inside region and a second outside region using the binary mask, where the second inside region defines an area of the second energy x-ray image or the second energy rib suppressed image inside the heart silhouette defined by the binary mask, and the second outside region defines an area of the second energy x-ray image or the second energy rib suppressed image outside the heart silhouette defined by the binary mask;

generating a registered inside region by registering the first inside region with the second inside region using free form deformation (FFD) registration;

generating a registered outside region by registering the first outside region with the second outside region using rigid deformation registration; and stitching the registered inside region with the registered outside region using soft weighting.

11. The non-transitory computer-readable storage device of claim 10, where registering the first inside region with the second inside region using FFD registration includes parameterizing a motion field between the first energy x-ray image and the second energy x-ray image, or between the first energy rib suppressed image and the second energy rib suppressed image, by interpolating a series of B-spline basis functions with a mesh of uniform spacing control points, and by minimizing a masked FFD registration cost function, where the masked FFD registration cost function is masked using the binary mask.

12. The non-transitory computer-readable storage device of claim 11, where generating the set of selectively filtered images includes filtering the first energy x-ray image or the first energy rib suppressed image using a Gaussian filter.

13. The non-transitory computer-readable storage device of claim 11, where generating the set of selectively filtered images includes filtering the second energy x-ray image or the second energy rib suppressed image using a vesselness operator using morphological suppression, or filtering the second energy x-ray image or the second energy rib suppressed image using a directional low pass filter.

14. The non-transitory computer-readable storage device of claim 13, where filtering the second energy x-ray image or the second energy rib suppressed image using a directional low pass filter includes:

generating a set of directional band-pass filters;

producing a vector of filter responses by convolving the second energy x-ray image or the second energy rib suppressed image with the set of directional band-pass filters, where a filter response is associated with a channel;

producing a transformed vector of filter responses by multiplying a filter response in the vector of filter responses by a weighting coefficient, where the weighting coefficient amplifies a selective width associated with the filter response or a selective direction associated with the filter response, or where the weighting coefficient suppresses the selective width associated with the filter response or the selective direction associated with the filter response; and filtering the second energy x-ray image or the second energy rib suppressed image based, at least in part, on the transformed vector of filter responses.

15. The non-transitory computer-readable storage device of claim 1, where generating the set of dual energy subtraction images includes correcting the set of selectively filtered images by removing scatter from a member of the set of selectively filtered images.

16. The non-transitory computer-readable storage device of claim 1, where generating the post-decomposition image includes applying un-sharp masking to the set of dual energy subtraction images, where the un-sharp masking is based, at least in part, on the set of dual energy subtraction images, an un-sharp coefficient, and a low-pass filtering operation, where the value of the un-sharp coefficient is within [0, 1).

17. The non-transitory computer readable storage device of claim 1, where generating the post-decomposition image includes selectively adjusting the dynamic range of the set of dual energy subtraction images to match, within a threshold amount, the dynamic range of a display device format or a storage device format.

18. The non-transitory computer-readable storage device of claim 1, where computing the coronary calcium score includes:

extracting a set of features from the post-decomposition image;

relating the set of features to a set of vessel-territory specific computed tomography (CT) calcium scores; and computing the coronary calcium score based, at least in part, on the relation of the set of features to the set of vessel-territory specific CT calcium scores.

19. The non-transitory computer-readable storage device of claim 18, where the set of features includes an exposure time feature, a vesselness filtering feature, a texture feature, a shape feature, or a curvedness feature.

20. The non-transitory computer-readable storage device of claim 18, where relating the set of features to the set of vessel-specific CT calcium scores is performed using a support vector machine (SVM) regression.

21. The non-transitory computer-readable storage device of claim 1, where the set of energy dependent images is acquired using switching, where the switching has a timing, where the timing of the switching is controlled by electrocardiograph (EKG) triggering.

22. The non-transitory computer-readable storage device of claim 21, where the EKG triggering is based upon a percentage of a running average of R-R wave intervals.

* * * * *